US010329552B2

(12) United States Patent
Mahan et al.

(10) Patent No.: US 10,329,552 B2
(45) Date of Patent: Jun. 25, 2019

(54) VACCINE FOR LIVESTOCK PRODUCTION SYSTEMS

(71) Applicant: The Regents of the University of California, Oakland, CA (US)

(72) Inventors: Michael Mahan, Santa Barbara, CA (US); Douglas Heithoff, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/507,160

(22) PCT Filed: Aug. 28, 2015

(86) PCT No.: PCT/US2015/047549
§ 371 (c)(1),
(2) Date: Feb. 27, 2017

(87) PCT Pub. No.: WO2016/033532
PCT Pub. Date: Mar. 3, 2016

(65) Prior Publication Data
US 2017/0267994 A1 Sep. 21, 2017

Related U.S. Application Data

(60) Provisional application No. 62/043,459, filed on Aug. 29, 2014.

(51) Int. Cl.
C12N 1/21 (2006.01)
C12N 15/09 (2006.01)
A61K 35/74 (2015.01)
C07K 14/255 (2006.01)
A01K 29/00 (2006.01)
A61K 39/112 (2006.01)
C12N 5/10 (2006.01)
C12N 15/01 (2006.01)
C12R 1/01 (2006.01)
C12R 1/42 (2006.01)
C12N 1/36 (2006.01)
A61K 39/00 (2006.01)

(52) U.S. Cl.
CPC ............ C12N 15/09 (2013.01); A01K 29/005 (2013.01); A61K 35/74 (2013.01); A61K 39/0275 (2013.01); C07K 14/255 (2013.01); C12N 1/36 (2013.01); C12N 5/10 (2013.01); C12N 15/01 (2013.01); C12R 1/01 (2013.01); C12R 1/42 (2013.01); A61K 39/00 (2013.01); A61K 2039/522 (2013.01)

(58) Field of Classification Search
None
See application file for complete search history.

(56) References Cited

U.S. PATENT DOCUMENTS

2002/0086032 A1  7/2002  Mahan
2003/0059442 A1  3/2003  Dougan
2010/0316058 A1  6/2010  Luo

FOREIGN PATENT DOCUMENTS

EP       1245679 A1    10/2002
WO    2002/26251       4/2002

OTHER PUBLICATIONS

Jazayeri, Seyed Davoud et al., Attenuated *Salmonellla typhimurium* SV4089 as potential carrier of oral DNA vaccine in chickens, Journal of Biomedicine and Biotechnology, 2012, pp. 1-8.
Alix (2008) Interplay between MgtC and PagC in *Salmonella enterica* serovar Typhimurium, Microbial Pathogenesis, 45: 236-240.
Aloui et al., (2010) Effects of dam and/or seqA mutations on the fatty acid and phospholipid membrane composition of *Salmonella enterica* serovar Typhimurium, Foodborne Pathogens and Disease, 7: 573-583.
Badie et al., (2007) Altered levels of *Salmonella* DNA adenine methylase are associated with defects in gene expression, motility, flagellar synthesis and bile resistance in the pathogenic strain 14028 but not in the laboratory strain LT2, Journal of Bacteriology, 189: 1556-1564.
Conner et al. (1998) Differential patterns of acquired virulence genes distinguish *Salmonella* strains. Proc Natl Acad Sci U S A.; 95:4641-5.
Curtiss et al. (2010) New technologies in using recombinant attenuated *Salmonella* vaccine vectors. Crit Rev Immunol; 30:255-70.
Donnenberg MS, Kaper JB. (1991) Construction of an eae deletion mutant of enteropathogenic *Escherichia coli* by using a positive-selection suicide vector. Infect Immun.; 59:4310-7.
Dueger et al. (2001) *Salmonella* DNA adenine methylase mutants elicit protective immune responses to homologous and heterologous serovars in chickens. Infect Immun.; 69:7950-4.
Dueger et al. (2003) *Salmonella* DNA adenine methylase mutants elicit early and late onset protective immune responses in calves. Vaccine.; 21:3249-58.
Dueger et al. (2003a) *Salmonella* DNA adenine methylase mutants prevent colonization of newly hatched chickens by homologous and heterologous serovars. Intl J Food Microbiol.; 80:153-9.
Glickman et al. (1978) Induced mutagenesis in dam-mutants of *Escherichia coli*: a role for 6-methyladenine residues in mutation avoidance. Mol Gen Genet.; 163:307-12.
Griggs T. (2005) Determining forage dry matter concentration with a microwave oven AG/Forage & Pasture/2005-01. 2005.
Harrison et al. (1997) Correlates of protection induced by live Aro-*Salmonella typhimurium* vaccines in the murine typhoid model. Immunology.; 90:618-25.
Hassan Jo, Curtiss R (1994), 3rd. Development and evaluation of an experimental vaccination program using a live avirulent *Salmonella typhimurium* strain to protect immunized chickens against challenge with homologous and heterologous *Salmonella* serotypes. Infect Immun.; 62:5519-27.
Hegazy et al. (2012) *Salmonella enterica* as a vaccine carrier, Future Microbiol. 7, 111-127.

(Continued)

*Primary Examiner* — Jennifer E Graser

(57) ABSTRACT

The invention relates to a live vaccine for protection against enteric bacterial infection.

25 Claims, 8 Drawing Sheets

(56) References Cited

OTHER PUBLICATIONS

Figure 1:
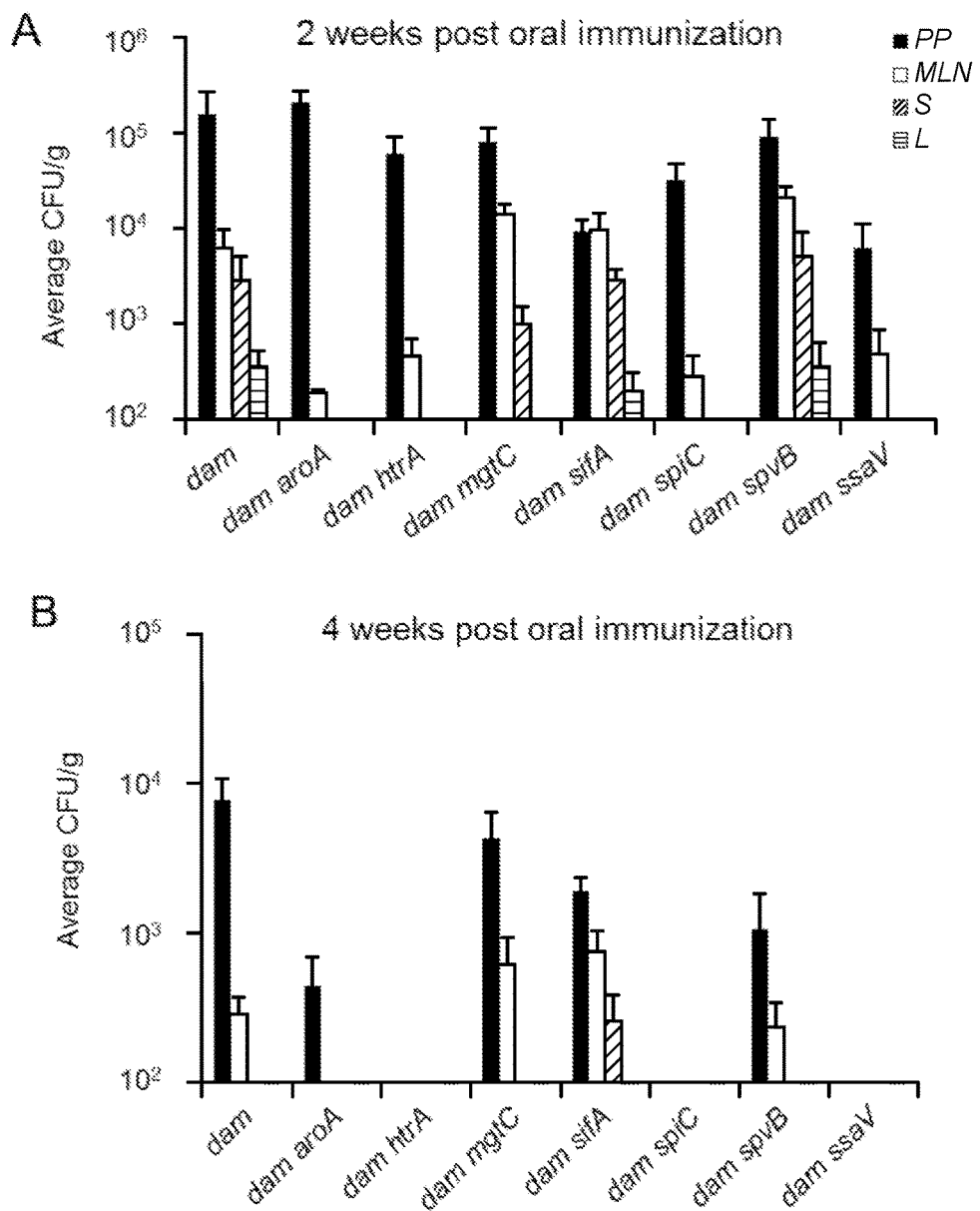

Heithoff et al. (1999) An essential role for DNA adenine methylation in bacterial virulence [see comments]. Science.; 284:967-70.
Heithoff et al. (2001) *Salmonella* DNA adenine methylase mutants confer cross-protective immunity. Infect Immun.; 69:6725-30.
Heithoff et al. (2007) In vivo-selected mutations in methyl-directed mismatch repair suppress the virulence attenuation of *Salmonella* dam mutant strains following intraperitoneal, but not oral, infection of naïve mice. J Bacteriol.; 189:4708-17.
Heithoff et al. (2008) Conditions that diminish myeloid-derived suppressor cell activities stimulate cross-protective immunity, Infect Immun. 76, 5191-5199.
Heithoff et al. (2008) Human *Salmonella* clinical isolates distinct from those of animal origin. Appl Environ Microbiol.; 74:1757-66.
Heithoff et al. (2012) Intraspecies variation in the emergence of hyperinfectious bacterial strains in nature. PLoS athogens.; 8:e1002647.
Hormaeche et al. (1991) Immunity conferred by *Aro-Salmonella* live vaccines. Microb Pathog.; 10:149-58.
Hormaeche et al. (1996) Protection against oral challenge three months after i.v. immunization of BALB/c mice with live *Aro Salmonella typhimurium* and *Salmonella enteritidis* vaccines is serotype (species)-dependent and only partially determined by the main LPS O antigen. Vaccine.; 14:251-9.
Jakomin et al (2008) Regulation of the *Salmonella enterica* std Fimbrial Operon by DNA Adenine Methylation, SeqA and Hdfr, Journal of Bacteriology, 190: 7406-7413.
Julio et al. (2001) DNA Adenine methylase is essential for viability and plays a role in the pathogenesis of Yersinia pseudotuberculosis and Vibrio cholerae. Infect Immun.; 69:7610-5.
Kong et al. (2011) Effect of deletion of genes involved in lipopolysaccharide core and O-antigen synthesis on virulence and immunogenicity of *Salmonella enterica* serovar Typhimurium. Infect Immun; 79:4227-39.
Li et al. (2009) Evaluation of new generation *Salmonella enterica* serovar Typhimurium vaccines with regulated delayed attenuation to induce immune responses against PspA. Proc Natl Acad Sci USA.; 106:593-8.
Mahan et al. (2012) *Salmonella* cross-protective vaccines: fast-forward to the next generation of food safety, Future Microbiol. 7, 805-808.
Mohler et al. (2006) Cross-protective immunity in calves conferred by a DNA adenine methylase vaccine *Salmonella enterica* serovar Typhimurium vaccine. Vaccine.; 24:1339.
Mohler et al. (2008) Cross-protective immunity conferred by a DNA adenine methylase deficient *Salmonella enterica* serovar Typhimurium vaccine in calves challenged with *Salmonella* serovar Newport. Vaccine.; 26:1751-8.
Mohler et al. (2011) Protective immunity conferred by a DNA adenine methylase deficient *Salmonella enterica* serovar Typhimurium vaccine when delivered in-water to sheep challenged with *Salmonella enterica* serovar Typhimurium. Vaccine.; 29:3571-82.
Mohler et al. (2012) Development of a novel in-water vaccination protocol for DNA adenine methylase deficient *Salmonella enterica* serovar Typhimurium vaccine in adult sheep. Vaccine.; 30:1481-91.
Nagy et al. (2008) "Gently rough": the vaccine potential of a *Salmonella enterica* regulatory lipopolysaccharide mutant. J Infect Dis; 198:1699-706.
Singh (2009) Salmonella vaccines for animals and birds and their future perspective. The Open Vaccine Journal, 2: 100-112.
Srikanth et al., (2011) *Salmonella* effector proteins and host-cell responses, Cellular and Molecular Life-sciences, 68: 3687-3697.

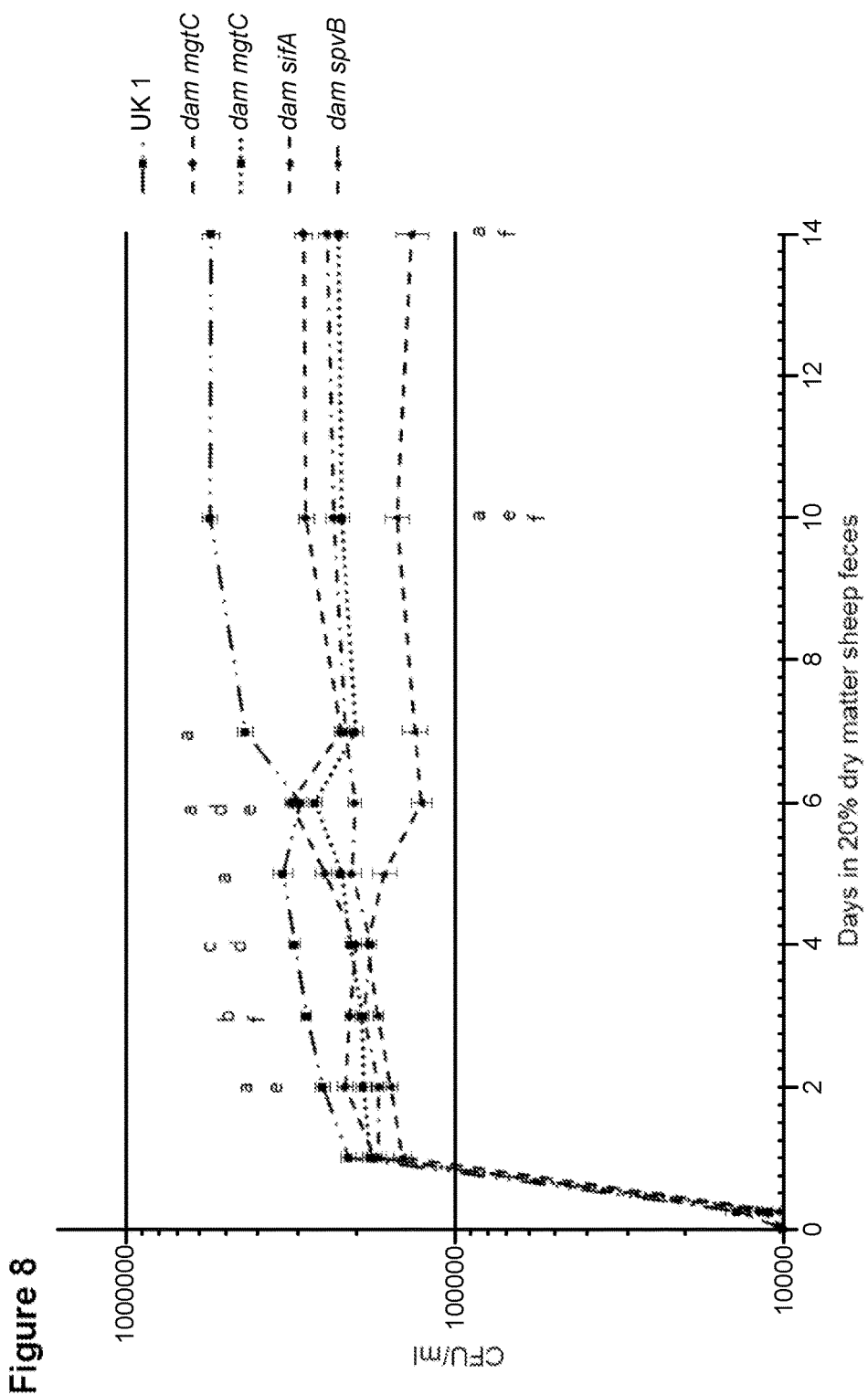

VACCINE FOR LIVESTOCK PRODUCTION SYSTEMS

CROSS-REFERENCE TO RELATED APPLICATIONS

This application is a National Stage Application under U.S.C. § 371 of and claims priority to PCT International Patent Application Number PCT/US2015/047549, entitled "Vaccine for Livestock Production Systems," filed on Aug. 28, 2015, which claims priority to U.S. Provisional Application No. 62/043,459, entitled "Vaccine for Livestock Production Systems," filed on Aug. 29, 2014, each of which is hereby incorporated by reference herein in its entirety.

FIELD OF THE INVENTION

The invention relates to a live vaccine for protection against enteric bacterial infection.

BACKGROUND OF THE INVENTION

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

Nontyphoidal *Salmonella* is the largest foodborne-disease burden in the United States, causing the most infections, hospitalizations and deaths, with 1.03 million illnesses reported annually. The economic burden associated with the disease is staggering, with the medical costs alone reaching more than $11 billion per year and substantial additional costs incurred by the food industry (recalls, litigation, reduced consumer confidence) and by state, local and federal public health agencies in response to NTS outbreaks. Globally, nontyphoidal *Salmonella* is estimated at 93.8 million cases and 155,000 deaths annually and has emerged as the leading cause of bacteremia in sub-Saharan Africa, where its fatality rate reaches up to 25%.

The health and economic burden associated with *Salmonella* is poised to worsen as the prolonged administration of antibiotics has resulted in the emergence of multidrug-resistant strains that have disseminated worldwide; e.g., S. *Typhimurium* DT104 has caused several food-borne disease outbreaks over the last two decades and is resistant to four of the five most commonly used antibiotics in veterinary medicine (tetracycline, β-lactams, aminoglycosides, and sulfonamides). These multidrug-resistant strains are oftentimes associated with more hospitalizations and bacteremia, and their maintenance in nature can occur at very low antibiotic concentrations that are commonly found in the environment including ground water. Further, a new class of carbapenem-resistant Enterobacteriaceae that are resistant to β-lactams, fluoroquinolones, and aminoglycosides was isolated from a patient in 2009, and such resistance has now shown widespread distribution among Gram-negative pathogens including *Salmonella*. Additionally, 'hypervirulent' *Salmonella* have been recently isolated (2012) from natural microbial populations derived from livestock. These hypervirulent strains are 100-times more virulent then most clinical isolates, are more capable of killing vaccinated animals, and are not detectable under standard laboratory test conditions due to rapid switching to a less-virulent state ex vivo. Together, these findings support the view that the *Salmonella* disease burden is poised to worsen with the potential emergence of more virulent multidrug-resistant strains that are difficult to control with currently available antibiotics.

*Salmonella enterica* is acquired via the fecal-oral route and is comprised of six subspecies that are subdivided into more than 2500 serovars (serological variants) based on carbohydrate, lipopolysaccharide (LPS), and flagellar composition, with subspecies *enterica* containing more than 99% of human pathogenic isolates. *S. enterica* infection can result in any of four distinct disease syndromes: enterocolitis/diarrhea, bacteremia, enteric (typhoid) fever and chronic asymptomatic carriage. Many serovars infect both humans and animals, and disease severity is a function of the serovar, strain virulence and host susceptibility.

*Salmonella* control efforts in livestock continue to be problematic for the following reasons: 1) most livestock infections are subclinical; 2) disease outbreaks are sporadic and frequently caused by specific serotypes although many serotypes are endemic to livestock production systems; 3) environmental persistence provides an ongoing reservoir for livestock infection; 4) the recent emergence of strain variants that are more virulent and can kill vaccinated animals; 5) some strains derived from human salmonellosis patients are distinct from those of animal origin; and 6) management and environmental events can increase pathogen exposure and/or compromise host immunity.

Vaccination represents a sustainable approach to any food safety plan, reducing pathogen exposure at the outset of the food production chain [1]. However, the immunity conferred by conventional vaccines is restricted to a narrow range of closely-related strains, and on-farm control requires the development of vaccines that elicit protection against many pathogenic serotypes [1]. Recent advancements have resulted in the development of modified live *Salmonella* cross-protective vaccines, many of which contain mutations in global regulatory networks that favor antigen production; and that are also suitable for the expression of heterologous antigens [2-6]. The molecular basis of cross-protective vaccine efficacy is not entirely clear. Relevant parameters might include: the expression of multiple antigens shared among pathogenic serotypes; diminished vaccine-induced immunosuppression; targeted removal of immunodominant antigens to expose cross-protective epitopes; type III secretion of recombinant antigens; and/or delayed vaccine attenuation for enhanced stimulation of immune responses (reviewed in [1, 3, 7, 8]).

Modified live attenuated *S. enterica* serovar *Typhimurium* that harbor loss of function mutations in genes may be useful for providing protection against a diversity of *salmonella*. The number of loci that might be considered for providing an applicable loss of function mutation is large, as is the number of applicable mutations at each locus. Some examples of loci for providing loss of function include loci involved in adherence, invasion, and intra- and extracellular survival of the bacteria (including many genes encoding proteins involved in metabolic processes). Some mutations of the gene encoding the DNA adenine methylase (dam) are capable of eliciting protection against a diversity of salmonellae. These appear to be well tolerated when applied as modified live vaccines in mice [2, 9], poultry [10, 11], sheep [12] and calves [13-15]. Induction of immunity is rapid and the vaccine can be administered with delivery via drinking water for low cost and low-stress immunization of livestock populations [12, 16].

The commercial success of any vaccine is dependent on the therapeutic index, the ratio of safety/toxicity, and safety is of particular concern for modified live vaccines that have the potential to revert to heightened virulence. Generally, a vaccine should satisfy 4 safety categories to be considered as a candidate for commercial use in a livestock production system. The relevant safety phenotypes are as follows: reduced i) vaccine shedding; ii) challenge strain shedding; iii) persistence in systemic tissues (liver/spleen); and iv) persistence in the environment.

It is understood that in providing an attenuated strain containing loss of function mutations, it is important that the improved safety profile arising from the relevant mutations does not decrease the efficacy of the vaccine in terms of the protection that it provides. Ultimately what one is looking for is a mutation that does not decrease the persistence of low level infection in the immunized individual and that does not increase the persistence of the immunogen in the environment when the pathogen is shed from the immunized animal and released to the environment.

It is difficult to predict which loss of function mutations are more useful for attenuation than others, particularly given that the data on potency and reversion to pathogenicity relevant to each locus and mutation arises from different laboratory systems.

A further complication is that it is desirable to select more than one locus for mutation, so as to prevent reversion to a pathogenic phenotype should at least one loss of function mutation be lost. Such an approach requires one to combine at least 2 loci from a large list of candidate loci and yet with limited guidance as to whether a particular combination is likely to increase or decrease the likelihood of reversion, or likely to increase or decrease the potency of the resulting attenuated vaccine.

There is a need for an attenuated live vaccine for protection against *Salmonella* infection.

There is also a need for an attenuated live vaccine for protection against *Salmonella* infection that has an improved safety phenotype.

There is a need for an attenuated live vaccine that has limited or no propensity for shedding from an animal, that has minimal persistence in the environment when shed from an animal, and that retains an acceptable level of persistence in an animal to invoke immunity.

SUMMARY OF THE INVENTION

The invention seeks to improve or address one or more of the above mentioned problems, limitations or needs and in one embodiment provides an enteric bacterium including:

a first loss of function mutation in a gene encoding DNA adenine methylase (herein dam) and a second loss of function mutation in a gene selected from the group consisting of: sifA, spvB and mgtC.

In a further embodiment there is provided a vaccine including:

an enteric bacterium as described above; and a carrier, diluent, excipient or adjuvant.

In a further embodiment there is provided a method of preventing or treating a bacterial enteric disease or condition including the step of providing a vaccine as described above to an individual in which a bacterial enteric disease or condition is to be prevented or treated.

In a further embodiment there is provided a method for producing a collection of immunogens suitable for use in a vaccine for preventing or treating a bacterial enteric disease or condition including:

providing an enteric bacterium having a loss of function mutation in dam, introducing a loss of function mutation into a gene of the bacterium selected from the group consisting of: sifA, spvB and mgtC.

In a further embodiment there is provided a method for producing a collection of immunogens suitable for use in a vaccine for preventing or treating a bacterial enteric disease or condition including:

providing an enteric bacterium having a loss of function mutation selected from the group consisting of: sifA, spvB and mgtC, introducing a loss of function mutation into the dam gene of the bacterium.

BRIEF DESCRIPTION OF THE DRAWINGS

FIG. 1. Evaluation of *Salmonella* dam double mutant vaccine candidates for colonization and persistence in mucosal and systemic tissues. BALB/c mice were orally immunized with S. *Typhimurium* UK-1 damΔ232 double mutant vaccine candidates (dam aroA [MT3138], dam htrA [MT3142], dam mgtC [MT3146], dam sifA [MT3150], dam spiC [MT3154], dam spvB [MT3158], dam ssaV [MT3162]) or the parental UK-1 damΔ232 vaccine strain (MT3134) ($10^9$ CFU). At 2 weeks (A) and 4 weeks (B) post oral immunisation, bacteria recovered from Peyer's patches (PP), mesenteric lymph nodes (MLN), liver (L) and spleen (S) were assessed for colony forming units (CFU) on LB medium. Limits of detection: PP, MLN, spleen <100 CFU; Liver <50 CFU.

FIG. 2. Homologous strain efficacy evaluation of *Salmonella* dam double mutant vaccine candidates. BALB/c mice were orally immunized with S. *Typhimurium* UK-1 damΔ232 double mutant vaccine candidates (dam aroA [MT3138], dam htrA [MT3142], dam mgtC [MT3146], dam sifA [MT3150], dam spiC [MT3154], dam spvB [MT3158], dam ssaV [MT3162]) or the parental UK-1 damΔ232 vaccine strain (MT3134) ($10^9$ CFU). Eleven weeks post-immunization, vaccinated mice were challenged with an oral dose of 200 $LD_{50}$ of homologous strain, wild-type S. *Typhimurium* UK-1 (χ3761). Non-vaccinated control mice all died by day 21 post-infection. Differences in the proportion of mice surviving virulent challenge was analysed using logistic regression (Genstat 15$^{th}$ edition [34]). Vaccination provided significant protection (P<0.01). Similar protection was afforded by the dam vaccines incorporating the secondary deletions mgtC, sifA and spvB as compared to the parent dam vaccine. A significant reduction in the efficacy of the dam vaccine was observed following introduction of the secondary deletions aroA, htrA, spiC and ssaV ( P<0.01; * P<0.001).

FIG. 3. Heterologous cross-protective efficacy evaluation of *Salmonella* dam double mutant vaccine candidates. BALB/c mice (16 to 25 per cohort) were orally immunized with *S. Typhimurium* UK-1 damΔ232 double mutant vaccine candidates (dam mgtC [MT3146], dam sifA [MT3150], dam spvB [MT3158]; $10^9$ CFU). Eleven weeks post-immunization, vaccinated mice were challenged with an oral dose of 100 $LD_{50}$ of heterologous *Salmonella* serotypes of clinical relevance to the livestock industry (*S. Dublin* 8895 [cattle], *S. Bovismorbificans* 225 [sheep], *S. Typhimurium* 131 [sheep]). Non-vaccinated control mice all died by day 21 post-infection. Differences in the proportion of mice surviving virulent challenge were analysed using logistic regression (GenStat 15$^{th}$ Edition, [34]). Vaccination with each of the dam vaccines incorporating the secondary deletions mgtC, sifA and spvB provided significant protection against the homologous and heterologous challenge strains assessed (*** P<0.001).

Figure 4:
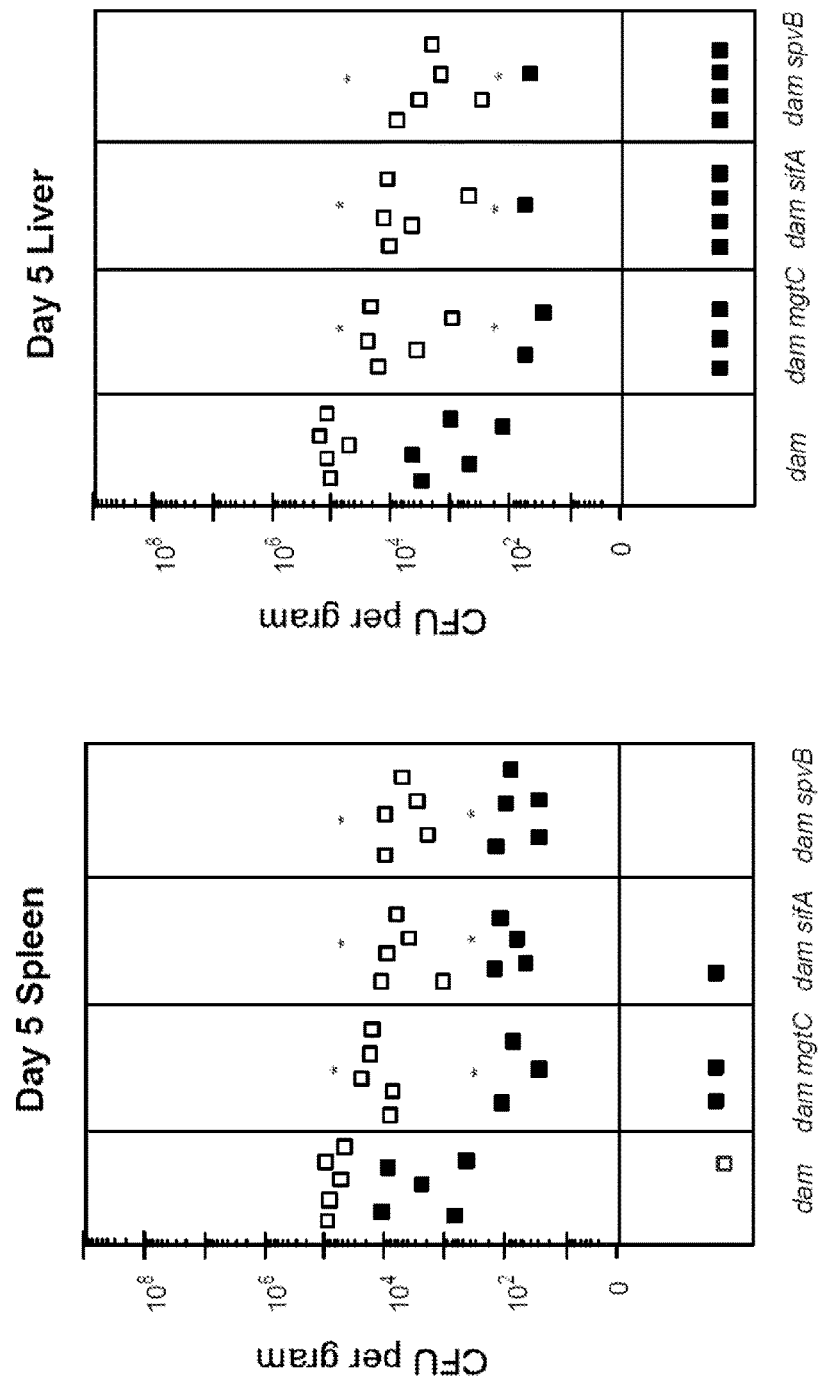

FIG. 4. Vaccine safety evaluation (reversion to 2-AP resistance) among *Salmonella* dam double mutant vaccine candidates. BALB/c mice were intraperitoneally infected with $10^5$ CFU of *S. Typhimurium* UK-1 damΔ232 double mutant vaccine candidates (dam mgtC [MT3146], dam sifA [MT3150], dam spvB [MT3158]) or the dam UK-1 parent vaccine strain [MT3134]. The number of 2-AP sensitive (open boxes) or 2-AP resistant (closed boxes) *Salmonella* organisms in the spleen (A) or liver (B) was enumerated at day 5 post-infection. The symbols below the zero CFU value represent the number of mice in which the bacterial load in spleen and liver was below the limit of detection (<25 CFU). Statistical significance for *S. Typhimurium* UK-1 dam double mutant vaccine persistence (2-AP$^s$) and reversion to heightened virulence (2-AP$^r$) in comparison to the parental *Salmonella* damΔ232 vaccine strain was determined using analysis of variance (* P<0.05).

Figure 5:
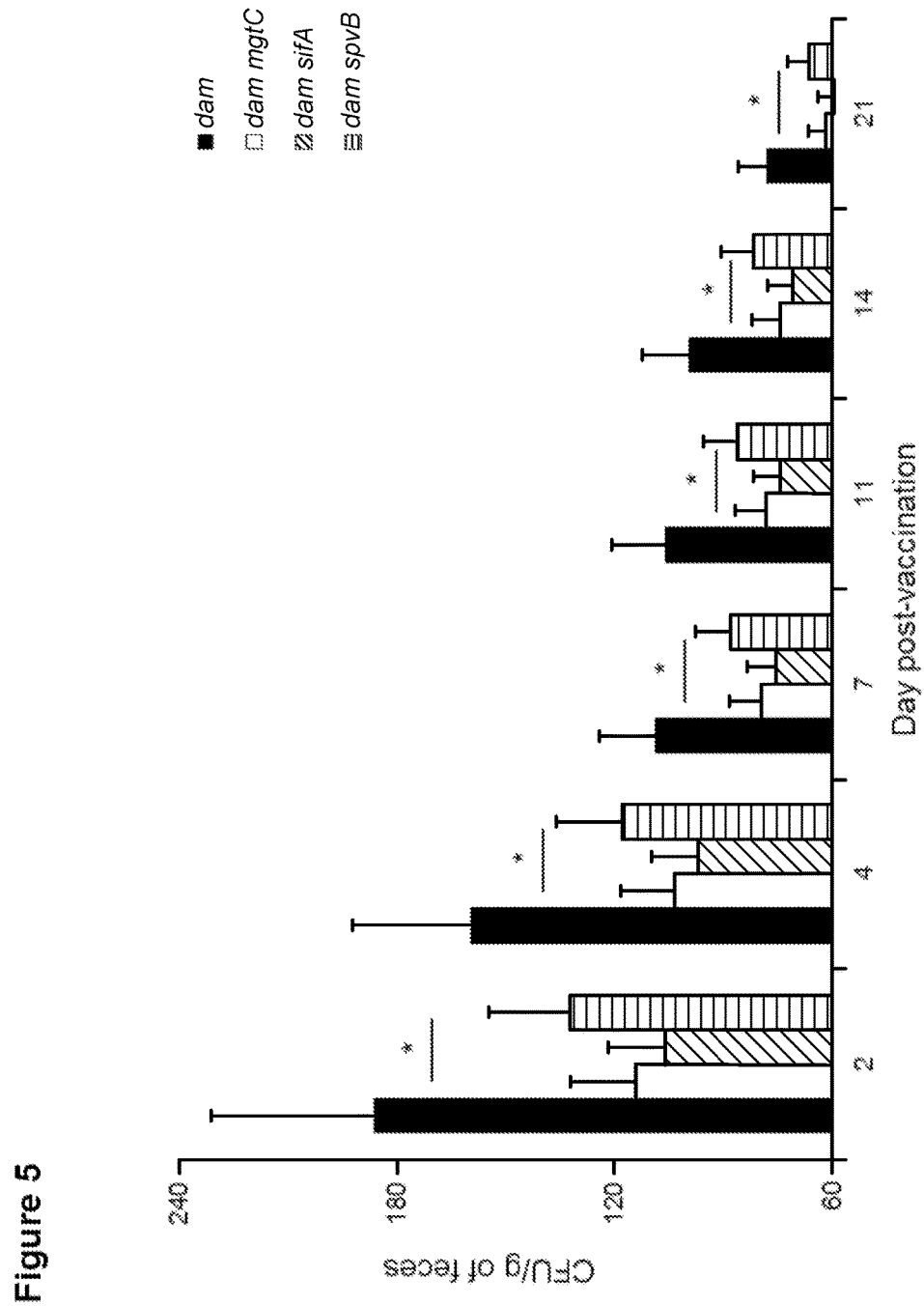

FIG. 5. Vaccine fecal shedding evaluation of *Salmonella* dam double mutant vaccine candidates. Kanamycin-resistant derivatives of *S. Typhimurium* UK-1 damΔ232 double mutant vaccine candidates, dam mgtC (MT3183), dam sifA (MT3184), dam spvB (MT3186), and the dam UK-1 parent strain (MT3180), were used to vaccinate BALB/c mice by the oral route ($10^9$ CFU). Feces was collected from individual mice and plated for CFU/g on kanamycin 50 μg/ml LB plates on days 2, 4, 7, 11, 14, and 21 post-immunization. Fecal shedding of the *Salmonella* dam double deletion vaccine candidates vs. the parental *Salmonella* damΔ232 vaccine strain was analysed using REML repeated measures analysis. Both vaccine and time following vaccination were significant (* P<0.05). No significant differences in fecal shedding were observed between the different double deletion dam vaccines. Values given are the model predicted mean number of CFU/g in feces of mice following vaccination. Limit of detection is 60 CFU.

Figure 6:
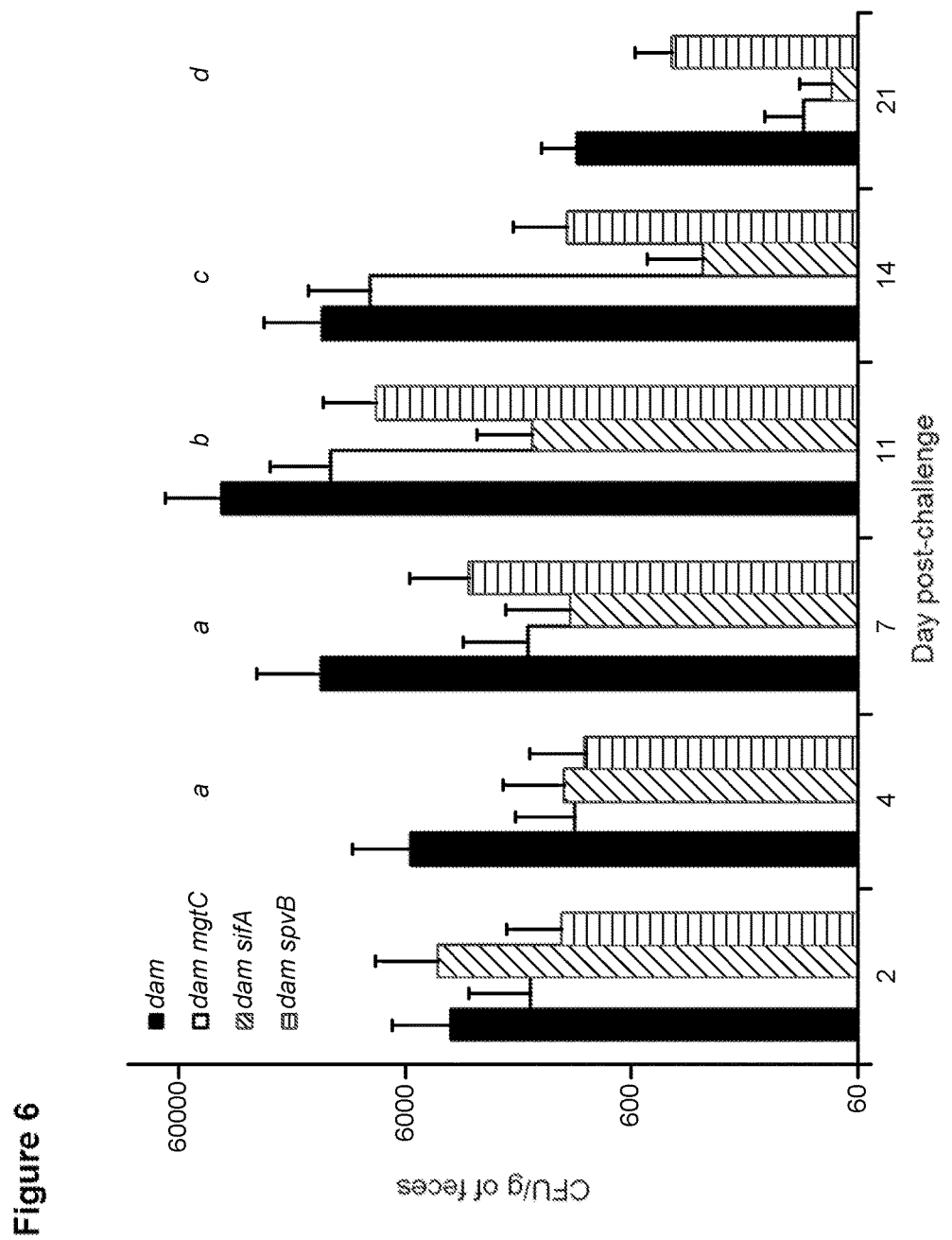

FIG. 6. Challenge strain fecal shedding in mice immunized with *Salmonella* dam double mutant vaccine candidates. Kanamycin-resistant derivatives of *S. Typhimurium* UK-1 damΔ232 double mutant vaccine candidates, dam mgtC (MT3183), dam sifA (MT3184), dam spvB (MT3186), and the dam UK-1 parent strain (MT3180), were used to vaccinate BALB/c mice by the oral route ($10^9$ CFU). Vaccine strain fecal clearance was achieved four weeks post-immunization. Eleven weeks post-immunization, vaccinated mice were challenged with a dose of 100 LD$_{50}$ of a kanamycin-resistant derivative of wild-type *S. Typhimurium* UK-1 (MT2315; $10^7$ CFU). Feces was collected from individual mice and plated for CFU/g on kanamycin 50 μg/ml LB plates on days 2, 4, 7, 11, 14, and 21 post-immunization. Fecal shedding of the wildtype challenge strain following challenge of vaccinated mice was analysed using REML repeated measures analysis. Both vaccine and time following vaccination were significant (* P<0.05) and there was a trend for significant interaction between time and vaccine (P=0.075). Pairwise comparisons revealed significant differences between groups at different times following virulent challenge; a=shedding of double deletion vaccines was significantly less than shedding of the parental dam vaccine; b=shedding of dam sifA and dam spvB vaccines was less than shedding of the parental dam vaccine and dam sifA shedding was significantly less than shedding of dam mgtC and dam spvB vaccines; c=shedding of dam sifA and dam spvB vaccines was significantly less than shedding of dam mgtC and dam spvB vaccines and shedding of dam spvB vaccine was significantly less than shedding of dam mgtC vaccine; d=shedding of dam sifA, dam spvB and dam mgtC vaccines was significantly less than shedding of dam spvB vaccine. Values given are model predicted mean CFU of wildtype challenge strain in feces following challenge. Limit of detection is 60 CFU.

Figure 7:
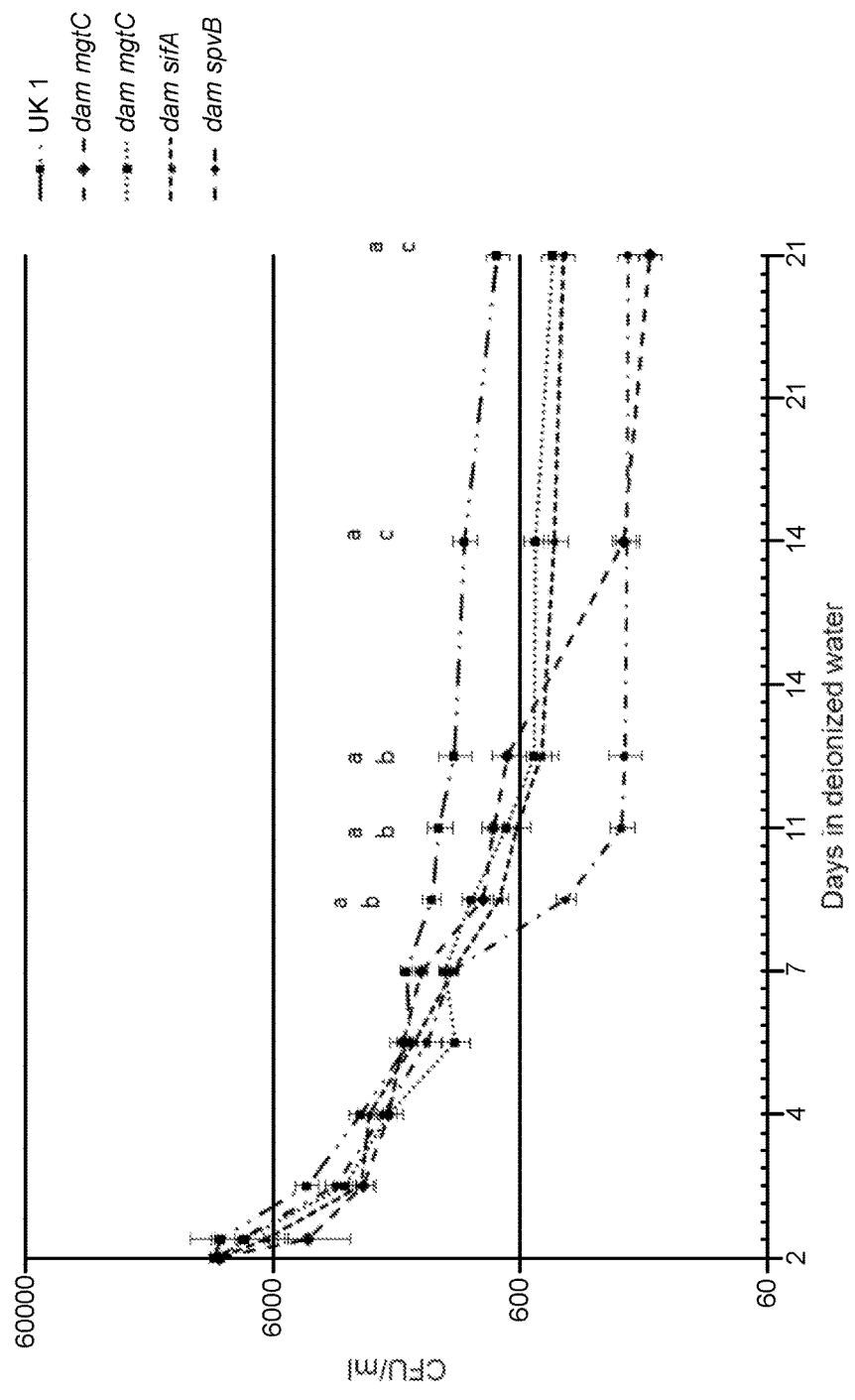

FIG. 7. Environmental vaccine persistence (deionized water) evaluation of *Salmonella* dam double mutant vaccine candidates. Kanamycin-resistant derivatives of *S. Typhimurium* UK-1 damΔ232 double mutant vaccine candidates, dam mgtC (MT3183), dam sifA (MT3184), dam spvB (MT3186), and the dam UK-1 parent strain (MT3180) were used to inoculate 20 ml of deionized water ($10^4$ CFU/ml). Triplicate assays were performed in 50 ml conical tubes with loose caps at room temperature. Samples were vortexed and plated for CFU/ml for a two week period at the time points indicated. Values given are the average CFU/ml with error bars indicating±standard error of the mean (SEM). The number of CFU/ml present in water over time was analysed using REML repeated measures analysis. A significant interaction between vaccine group and time was observed (P<0.001). Pairwise comparisons revealed significant differences between groups at different times (P<0.05). a=all vaccines have lower CFU/ml than the parent UK-1 wild type strain; b=the CFU/ml for the dam Δ232 strain is significantly less than the CFU/ml for the dam mgtC, dam sifA and dam spvB strains; c=CFU/ml for the dam Δ232 and dam spvB strains were significantly less than for the dam sifA and dam mgtC strains.

FIG. 8. Environmental vaccine persistence (sheep feces) evaluation of *Salmonella* dam double mutant vaccine candidates. Twenty percent fecal dry matter was generated by adding 20 ml of deionized water to 5 g of dried sheep feces (gift from Barbara Byrne, University of California, Davis; [32,33]). The 20% fecal dry matter was inoculated ($10^4$ CFU/ml) with kanamycin-resistant derivatives of *S. Typhimurium* UK-1 damΔ232 double mutant vaccine candidates, dam mgtC (MT3183), dam sifA (MT3184), dam spvB (MT3186), or the dam UK-1 parent strain (MT3180). Triplicate assays were performed in 50 ml conical tubes with loose caps at room temperature. Samples were vortexed and plated for CFU/ml for a two week period at the time points indicated. Values given are the average CFU/ml with error bars indicating±standard error of the mean (SEM). The number of CFU/ml present in feces over time was analysed using REML repeated measures analysis. A significant interaction between vaccine group and time was observed (P<0.001). Pairwise comparisons revealed significant differences between groups at different times (P<0.05). CFU/ml for all vaccine strains were less than for the parent UK-1 wild type for all time points except for day 1 and 6. a=dam sifA significantly less than dam, dam mgtC and dam spvB; b=dam sifA significantly less than dam and dam mgtC; c=dam sifA significantly less than dam mgtC; d=dam spvB significantly less than dam mgtC; e=dam spvB significantly less than dam; f=dam mgtC significantly less than dam.

DETAILED DESCRIPTION OF THE EMBODIMENTS

As discussed above, enteric bacterial disease, for example gastroenteritis and other conditions characterised by diarrhoea, fever, and dehydration remain as major problems in livestock production. *Salmonella* infection, and salmonellosis are of key concern. To date all of the attempts to prevent or treat these conditions in livestock animals have met with limited success, either because of comprised or limited potency of the vaccine or comprised safety profile. Of particular concern has been vaccines that are shed from the animal and that persist in the environment.

The challenge has been to provide an attenuated bacterium that is sufficiently robust so as to be able to persist in a livestock animal, thereby providing immunity, and that has limited potential for shedding and persistence in feces and more generally the environment, such as a feedlot or other part of the livestock production chain. The need to provide double mutation to prevent reversion to a pathogenic phenotype is an additional level of complexity, particularly where a very large number of candidate genes for inactivation are known.

The inventors have been interested to provide enteric bacteria useful as live immunogens for example in an attenuated live vaccine, that have an improved safety profile or phenotype, insofar as having a lesser likelihood of reversion to a pathogenic phenotype, a lesser likelihood of shedding, and lesser likelihood of persistence in the environment. From an extensive list of potential candidate loci, the inventors have identified 3 loci that can be used to introduce a loss of function mutation in a dam inactivated strain to provide an attenuated microorganism that has a desirable safety profile, while retaining potency to protect against or treat a broad range of enteric bacteria, and in particular a broad range of *Salmonella*.

A. Definitions

'Loss of function mutation' generally refers to a mutation of a gene that completely or partially inactivates a relevant function of the gene in a given biological process. Particular loss of function mutations of interest are those that interrupt the lifecycle of enteric bacteria in a host, while not disrupting the immunogenic profile of the bacteria.

'Enteric bacteria' generally refers to bacteria of the intestines or gut. Of particular interest are the 'Enterobacteriaceae', a large family of Gram-negative enteric bacteria that includes pathogens, such as *Salmonella, Escherichia coli, Yersinia pestis, Klebsiella* and *Shigella*. Other disease-causing bacteria in this family include *Proteus, Enterobacter, Serratia*, and *Citrobacter*.

'*Salmonella*' is an enteric bacteria of the Enterobacteriaceae.

'dam' refers to the gene encoding DNA adenine methylase, also known as deoxyadenosine methylase, DNA adenine methyltransferase or deoxyadenosyl methyltransferase. An example of an accession number for the *S. Typhimurium* dam gene is NCBI accession number: 1255007. The locus tag for this gene is STM3484.

'sifA' refers to the gene encoding the secreted effector protein SifA. An example of an accession number for the *S. Typhimurium* sifA gene is NCBI accession number 1252742. The locus tag for this gene is STM 1224.

'spvB' refers to the gene encoding the *Salmonella* plasmid virulence protein B (SpvB). An example of an accession number for the *S. Typhimurium* spvB gene is NCBI accession number 1256199. The locus tag for this gene is PSLT039.

'mgtC' refers to the gene encoding Mg(2+) transport ATPase protein C, MgtC. An example of an accession number for the *S. Typhimurium* mgtC gene is NCBI accession number 1255288. The locus tag for this gene is STM3764.

'attenuated' for example, in "attenuated bacteria" generally refers to a modification of a bacterium that reduces the virulence of the bacterium, but still keeps it viable (or "live")

so that it can replicate, albeit at a slower rate or under different conditions. Attenuation takes an infectious agent and alters it so that it becomes harmless or less virulent. Typically, attenuation does not substantially decrease the immunogenicity of the relevant bacteria.

'vaccine' generally refers to a composition that contains an immunogen i.e. a substance capable of invoking an immune response. Typically a vaccine is useful for immunising, preventing or providing protection against infection, or manifestation of a relevant symptom, on exposure to a pathogen, particularly where the exposure is in the form of challenge. A vaccine may be used for prevention or for treatment of a condition. A vaccine may be used to minimise the likelihood of infection with a pathogen.

'bacterial enteric disease or condition' generally refers to a condition arising from the infection of an individual with enteric bacteria. Such a condition may include the following symptoms: gastric inflammation, dehydration, diarrhoea, fever. Salmonellosis is one example of a bacterial enteric disease or condition.

'immunisation' as used herein, generally refers to a process by which a subject's immune system is fortified against an immunogen. The attenuated *Salmonella* microorganisms of the invention have utility in immunising a subject against Salmonellaw and thereby prevent infection with other, more virulent *Salmonella* serovars.

'gene' as used herein, refers to the coding sequence and its regulatory sequences such as promoter and termination signals.

'comprise' and variations of the term, such as 'comprising', 'comprises' and 'comprised', are not intended to exclude further additives, components, integers or steps.

The present inventors have found that specific combinations of loss of function mutations in *Salmonella* genes provide a particular advantage in the generation of live attenuated strains of *Salmonella* which have utility as live vaccines for conferring immunity from infection with virulent or pathogenic serotypes of *Salmonella*.

Specifically, the inventors have found that the introduction of mutations in the sifA, spvB or mgtC genes in a strain of *Salmonella* also having a loss of function mutation in the dam gene, results in the generation of microorganisms which can be safely administered to subjects, are safe in the environment and maintain the capacity to confer protection to heterologous pathogenic serotypes of *Salmonella*.

The present invention thus provides a live attenuated *Salmonella* microorganism, wherein said microorganism comprises a loss of function mutation in the dam gene and at least one further loss of function mutation in a gene selected from the group consisting of: sifA, spvB and mgtC.

In a particularly preferred embodiment, the microorganism according to the invention has a loss of function mutation in dam and a further loss of function mutation in sifA. In this embodiment, the microorganism or enteric bacteria may not have a loss of function mutation in spvB or mgtC.

The attenuated *Salmonella* microorganisms of the present invention can be prepared by known techniques, e.g., by deletion mutagenesis, insertional inactivation or substitution of one or more nucleotides in the target genes. The skilled person will appreciate that the target genes do not necessarily need to be mutated, provided that the expression of the native gene product is in some way disrupted. For example, the mutation may be made upstream of the target gene, for example in a promoter or regulatory region.

In one embodiment, the loss-of-function mutations engineered into dam, sifA, mgtC and spvB genes are in-frame deletions. The use of in-frame deletions is such that the transcription of downstream genes is maintained.

Other suitable techniques include the use of a suicide vector comprising a mutated gene and a selective marker. The suicide vector is introduced into the *Salmonella* microorganism carrying the wild-type gene sequence (although, as the skilled person will appreciate, may comprise one or more mutations at alternative loci) by conjugation. The wild-type gene is replaced with the mutated gene via homologous recombination, and the mutated microorganism is identified using the selective marker. Other suitable techniques are described, for example, in WO 1996/17951.

The skilled person will also be able to readily determine whether the introduced mutation has resulted in a loss of function or if gene function is impaired. For example, the mgtC gene is required for survival of *Salmonella* in environments having low magnesium concentration.

The loss of function mutations introduced into the dam gene and any one of the sifA, spvB or mgtC genes are effective for resulting in attenuation of the microorganism.

Preferably the microorganism is an enteric bacterium, and in particular a pathogenic enteric bacterium, such as a member of Enterobacteriacea.

Most preferably the microorganism is *Salmonella*. It will be appreciated by the skilled person, that any number of *Salmonella* serotypes which are normally virulent or pathogenic, can be treated using the above techniques to generate live attenuated strains. For example, the *Salmonella* microorganisms may be from a wide variety of *Salmonella enterica* subsp. *Enterica serovars*, including, but not limited to serovars *S. Typhimurium, S. Enteritidis, S. Dublin, S. Newport, S. Choleraesuis,* or *S. Bovismorbificans*. In a particularly preferred embodiment, the loss of function mutations are introduced into an *S. Typhimurium* microorganism.

In yet a further preferred embodiment, the attenuated live microorganism is an *S. Typhimurium* having loss of function mutations in both dam and sifA genes.

The inventors have found that the microorganisms of the present invention are particularly suitable for use as vaccines for immunising subjects against virulent serotypes of *Salmonella* and minimising the likelihood of infection with virulent serotypes. In particular, the inventors have found that compared with *Salmonella* having loss of function mutations in other combinations of genes, *Salmonella* having mutations in the dam gene as well as in any of the sifA, spvB or mgtC genes, exhibited improved vaccine safety in the subject to be immunised and in the environment.

Thus, in a further aspect, the present invention provides a vaccine composition for inducing an immune response in a subject to an enteric bacteria, preferably a pathogenic bacteria such as *Salmonella*. The vaccine composition comprises a live attenuated *Salmonella* microorganism in an amount sufficient to elicit an immune response in the subject and a suitable carrier or diluent, wherein said live attenuated microorganism comprises a loss of function mutation in the dam gene and at least one further loss of function mutation in a gene selected from the group consisting of: sifA, spvB and mgtC.

In a particularly preferred embodiment, the vaccine composition comprises an amount of a live attenuated *Salmonella* comprising loss of function mutations in both the dam and sifA genes.

To formulate the vaccine compositions, the attenuated microorganisms may be present in the composition together with any suitable excipient. For example, the compositions may comprise any suitable adjuvant. Furthermore, the compositions may be adapted for a variety of means of administration. Preferred administration routes include the oral, mucosal (e.g., nasal) or systemic routes (e.g. parenteral injection) and the vaccines are live attenuated *Salmonella* microorganisms. In one particular embodiment, the vaccine compositions can be provided for inclusion in the drinking water or food or feedlot of the subject to which it is to be delivered.

The number of attenuated microorganisms present in the vaccine compositions can readily be determined by the skilled person, depending on the intended route of administration of the vaccine composition and the subject to which it will ultimately be delivered.

The particular suitable carriers or diluents employed in the vaccine compositions are not critical to the present invention and are conventional in the art. Examples of diluents include: buffer for buffering against gastric acid in the stomach, such as citrate buffer (pH 7.0) containing sucrose, bicarbonate buffer (pH 7.0) alone, or bicarbonate buffer (pH 7.0) containing ascorbic acid, lactose and optionally aspartame. Examples of carriers include: proteins, e.g., as found in skimmed milk; sugars, e.g., sucrose; or polyvinylpyrrolidone.

The present inventors have found that administration of the attenuated microorganisms of the present invention or vaccine compositions comprising the same to a subject, confers resistance in that subject to subsequent infection with a wild-type or pathogenic serovar.

Accordingly, in yet a further aspect, the present invention provides a method of preventing infection with a virulent strain of *Salmonella*, said method comprising:
administering to a subject in need thereof:
an amount of a live attenuated *Salmonella* microorganism, wherein said microorganism comprises a loss of function mutation in the dam gene and at least one further loss of function mutation in a gene selected from the group consisting of: sifA, spvB and mgtC, or
a vaccine composition comprising a live attenuated *Salmonella* microorganism and a suitable carrier or diluent, wherein said live attenuated microorganism comprises a loss of function mutation in the dam gene and at least one further loss of function mutation in a gene selected from the group consisting of: sifA, spvB and mgtC.
wherein the amount of microorganism or vaccine administered is sufficient to elicit an immune response in the subject.

It will be appreciated that in preventing infection with a virulent strain of *Salmonella*, the present invention also provides a method of immunising a subject against infection with a virulent serovar of *Salmonella*.

The attenuated microorganisms of the invention and vaccine compositions comprising the same are suitable for immunising subjects against infection with virulent and pathogenic serovars of *Salmonella* which normally result in salmonellosis. The attenuated microorganisms of the invention and vaccine compositions comprising the same are particularly suitable for immunising any animal which is susceptible to infection with *Salmonella* microorganisms. For example, in some embodiments, the subjects which can be immunised may be humans. Alternatively, the subjects to be immunised may be veterinary species and livestock. Examples of subjects to be immunised in accordance with the present invention include pigs, sheep, calves, cattle, deer, goats, camels, horses, chicken, turkey, ducks, quails etc.

The amount or number of attenuated *Salmonella* microorganisms or vaccine can readily be determined by the skilled person. In general, about $10^2$ cfu to about $10^{10}$ cfu, preferably about $10^5$ to about $10^{10}$ cfu of microorganism is administered. An immunising dose varies according to the route of administration. The skilled person will appreciate that the effective dose for a vaccine administered parenterally (for example, by intravenous, intraperitoneal or subcutaneous injection) is likely to be smaller than a similar vaccine which is administered orally, for example in drinking water or in food.

By an 'immunising amount' as used herein, is meant an amount that is able to induce a protective immune response in the subject that receives the attenuated microorganism or vaccine comprising the same. The immune response may be a humoral, mucosal, local and/or cellular immune response. Further, as the skilled person will appreciate, the amount of attenuated microorganism or vaccine required will also depend on age, weight and other factors relating to the subject being immunised.

The skilled person will appreciate that in order to produce sufficient numbers of the live attenuated microorganism described herein, it may be necessary to culture the microorganism in suitable conditions. For example, depending on the intended route of administration of the microorganism, it may be necessary to culture the microorganism under aerobic or anaerobic conditions. The skilled person will be readily be able to determine the relevant culturing conditions. Furthermore, it may be desirable, once sufficient numbers of the microorganism have been produced in culture (for example, once the microorganism has reach log-phase growth), to purify the culture to remove any elements of the growth medium which are not intended for inclusion in downstream use of the microorganism.

Accordingly, in one embodiment, the present invention provides a purified culture of a live attenuated *Salmonella* microorganism as described above.

The culture comprising the live attenuated *Salmonella* microorganism may be purified so that it may be used in downstream applications including for use as a vaccine or in the manufacture of a vaccine composition to induce an immune response in a subject to a *Salmonella* microorganism.

It will be appreciated that the purified culture may be freeze dried, frozen or reconstituted, depending on the intended downstream application of the culture.

Further aspects of the present invention and further embodiments of the aspects described in the preceding paragraphs will become apparent from the following description, given by way of example and with reference to the accompanying drawings.

It will be understood that the invention disclosed and defined in this specification extends to all alternative combinations of two or more of the individual features mentioned or evident from the text or drawings. All of these different combinations constitute various alternative aspects of the invention. All patents, patent applications, and publications cited in this specification are herein incorporated by reference in their entirety to the same extent as if each independent patent application, or publication was specifically and individually indicated to be incorporated by reference.

EXAMPLES

1. Materials and Methods
1.1. Bacterial Strains and Growth Conditions

*Salmonella* animal isolates were derived from different outbreaks, individual cases, or surveillance submissions to diagnostic laboratories [31]. Virulent *S. Typhimurium* UK-1 was used in all studies for comparison [17]. Unless otherwise specified, bacteria were derived from stationary phase cultures aerated at 37° C. containing Luria-Bertani (LB) medium [18]. Antibiotics were used at the following concentrations: kanamycin (Kn), 50 µg/ml, ampicillin (Ap), 50 µg/ml.

1.2. Construction of *S. Typhimurium* Dam Vaccine Candidates Comprising an Additional Attenuating Mutation

*S. Typhimurium* UK-1 Adam was constructed by introducing an in-frame 300 bp deletion of defined dam sequence, termed damΔ232 [19], using standard genetic protocols [20]. The resultant *S. Typhimurium* UK-1 damΔ232 strain (MT3134) was shown to be sensitive to the purine analog, 2-aminopurine (2-AP), which is toxic to strains lacking a non-functional DNA adenine methylase [21, 22], and was used as the parental *Salmonella* dam vaccine strain for all studies. Secondary virulence-attenuating deletion mutations were introduced into the parental *S. Typhimurium* UK-1 damΔ232 strain utilizing suicide vector pCVD442 as described [20], resulting in the construction of in-frame deletions of defined coding sequence in the following targeted genes: dam aroA (MT3138; 1056 bp deletion); dam htrA (MT3142; 1341 bp deletion); dam mgtC (MT3146; 606 bp deletion); dam sifA (MT3150; 807 bp deletion); dam spiC (MT3154; 306 bp deletion); dam spvB (MT3158; 1563 bp deletion); and dam ssaV (MT3162; 1959 bp deletion). The resultant genetic constructs were confirmed by PCR using primers that flank the deleted sequences.

1.3. Virulence and Protection Assays

Oral and Intraperitoneal Lethal Dose$_{50}$ (LD$_{50}$): The dose required to kill 50% of infected animals was determined via the oral (via gastrointubation) and intraperitoneal (i.p.) routes by infecting at least 10 mice [30, 19]. *Salmonella* test strains and wild-type *S. Typhimurium* reference strain 14028 were grown overnight in LB medium. Bacterial cells resuspended in 0.2 ml of 0.2M Na$_2$HPO4 pH 8.1 or 0.1 ml of 0.15M NaCl (for oral and i.p. administration, respectively) were used to infect mice, which were examined daily for morbidity and mortality up to 3 weeks post infection. The oral and i.p. LD$_{50}$ for *S. Typhimurium* UK-1 is $10^5$ and <10 organisms, respectively [30]. Six-to-eight week old BALB/c mice were used in all virulence studies. Protection assays. Mice were orally immunized with *S. Typhimurium* dam vaccine strains at a dose of $10^9$ CFU [30, 19]. To avoid transient, non-specific cross-protective immune responses attributed to the persistence of the vaccine strain within host tissues [23-25], immunized mice were not challenged with virulent *Salmonella* until 4 to 5 weeks after the vaccine strain was cleared from mucosal (Peyer's patches; mesenteric lymph nodes) and systemic tissues (liver; spleen) of immunized animals. Eleven weeks post-immunization, mice were orally challenged with virulent *Salmonella enterica* serotypes at an infection dose equivalent to 100- to 200-fold LD$_{50}$. Mice were examined daily following challenge for morbidity and mortality for up to 3 weeks post-challenge.

1.4. Construction of Antibiotic Resistant Derivatives of *Salmonella* Vaccine Candidates to Assess Vaccine and Challenge Strain Fecal Shedding, and Persistence within Deionized Water and Sheep Feces Kanamycin resistant (Kn$^r$) derivatives of *S. Typhimurium* UK-1 damΔ232 double mutant vaccine candidates were constructed to assess vaccine fecal shedding. *S. Typhimurium* strain MT2057 is a Kn$^r$ derivative of wild-type reference strain 14028, containing a Lac$^k$ MudJ transcriptional fusion encoding Kn$^r$ which is used to discern it from other

*Salmonella* that are inherently Lac⁻ [19, 26]. Phage P22 grown on donor strain MT2057 was used to transduce recipient *Salmonella* dam vaccine candidates to kanamycin resistance [18], generating Kn$^r$ *S. Typhimurium* UK-1 damΔ232 double mutant vaccine candidates, dam mgtC (MT3183), dam sifA (MT3184), dam spvB (MT3186), and the dam UK-1 parent strain (MT3180). Vaccine strain shedding. BALB/c mice were vaccinated with Kn$^r$ *S. Typhimurium* UK-1 dam double mutant vaccine candidates by the oral route ($10^9$ CFU). Feces was collected from individual mice and plated for CFU/g on kanamycin 50 µg/ml LB plates on Days 2, 4, 7, 11, 14, and 21 post-immunization. Challenge strain shedding. BALB/c mice were vaccinated with Kn$^r$ *S. Typhimurium* UK-1 dam double mutant vaccine candidates by the oral route ($10^9$ CFU). Vaccine strain fecal clearance occurred by four weeks post immunization. Eleven weeks post-immunization, vaccinated mice were challenged with a dose of 100 $LD_{50}$ of Kn$^r$ derivative of *S. Typhimurium* UK-1 (MT2315; $10^7$ CFU). Feces was collected from individual mice and plated for CFU/g on kanamycin 50 µg/ml LB plates on Days 2, 4, 7, 11, 14, and 21 post-immunization. Persistence within de-ionized water and sheep feces. Twenty percent fecal dry matter was prepared by adding 20 ml of deionized water to 5 g of dried sheep feces (gift from Barbara Byrne, University of California, Davis; [27, 28]). De-ionized water (20 ml) and 20% sheep feces was inoculated with Kn$^r$ derivatives of *S. Typhimurium* UK-1 damΔ232 double mutant vaccine candidates, dam mgtC (MT3183), dam sifA (MT3184), dam spvB (MT3186), or the dam UK-1 parent strain (MT3180) ($2\times10^5$ CFU). Triplicate assays were performed in 50 ml conical tubes with loose caps at room temperature. Samples were vortexed and plated for CFUs over a two week period.

1.5 Statistical Analysis

Continuous repeated measures data were analyzed using residual (or restricted) maximum likelihood (REML) analysis (Genstat, 15th Edition, VSN International, UK, [34]). A single variate, repeated measures model was fitted for the factors time and treatment for the variable CFU. The Wald chi-square test was used to determine significant individual effects and or significant interactions between factors. Any non-significant terms were dropped from the model and analysis repeated. Following analysis data are presented as predicted model based means. Predicted means are those obtained from the fitted model rather than the raw sample means. This is important as predicted means represent means adjusted to a common set of variables, thus allowing valid comparison between means. A P value less than 0.05 was considered to be statistically significant. The number of CFU present in tissues at necropsy was analysed using analysis of variance (ANOVA, Genstat, 15th Edition, VSN International, UK). Differences between the individual means calculated using REML and ANOVA were determined by calculating an approximate least significant difference (LSD). A difference of means that exceeded the calculated LSD was considered significant.

Binomial data (shedding [yes/no] and outcome [live/dead]) were analyzed using a logistic regression model (Genstat, 15th Edition, VSN International, UK, [34]). Vaccine was fitted to the model. Overall significance was assessed using the Wald statistic (P<0.05). Significance of fixed effects (vaccine) was assessed according to the t parameter estimates relative to the reference group. P values less than 0.05 were considered statistically significant.

1.6. Ethics Statement

All animal experimentation was conducted following the National Institutes of Health guidelines for housing and care of laboratory animals and performed in accordance with Institutional regulations after pertinent review and approval by the Institutional Animal Care and Use Committee at the University of California, Santa Barbara.

2. Results 2.1. Construction of *Salmonella* Dam Vaccine Candidates Containing a Secondary Virulence-Attenuating Mutation The commercial success of modified live vaccines is dependent upon the therapeutic index, the ratio of safety/efficacy and, thus, secondary virulence-attenuating mutations were introduced into the *S. enterica* serovar *Typhimurium* dam vaccine to improve vaccine safety. An antibiotic sensitive, dam-deletion derivative of parental strain UK-1 was constructed to eliminate the potential transmission of antibiotic resistance to other microbial strains (Materials and Methods). The resultant *S. Typhimurium* UK-1 damΔ232 (MT3134) was used as the parental vaccine background for all studies. Secondary virulence-attenuating mutations were subsequently introduced into *S. Typhimurium* UK-1 damΔ232 to improve vaccine safety (Materials and Methods). These mutations were targeted to genes involved in intracellular and/or systemic survival, including aroA (amino acid biosynthesis); htrA (stress response); mgtC (magnesium transport); sifA, spiC, ssaV (*Salmonella* Pathogenicity Island-2 (SPI-2); and spvB (cytotoxin production). The resultant *Salmonella* dam double mutant vaccine candidates, dam aroA, dam htrA, dam mgtC, dam sifA, dam spiC, dam spvB, dam ssaV, were subsequently evaluated for improved safety/efficacy in comparison to the parental *Salmonella* dam vaccine strain.

2.2. Evaluation of *Salmonella* Dam Double Mutant Vaccine Candidates for Colonization and Persistence in Mucosal and Systemic Tissues A principal concern of introducing secondary virulence-attenuating mutations into modified live vaccines is the potential of loss of efficacy due to reduced antigen exposure as a consequence of accelerated vaccine clearance. Thus, the *S. Typhimurium* UK-1 damΔ232 double mutant vaccine candidates, dam aroA, dam htrA, dam mgtC, dam sifA, dam spiC, dam spvB, dam ssaV, were examined for those that maintained colonization and persistence parameters similar to those found in the parental *S. Typhimurium* UK-1 damΔ232 vaccine strain. BALB/c mice were orally infected with the *Salmonella* dam double mutant vaccine candidates ($10^9$ CFU), and colonization/persistence of the vaccine strains was assessed in mucosal (Peyer's patches; mesenteric lymph nodes) and systemic tissues (liver and spleen) at 2 and 4 weeks post infection (FIG. 1). The *Salmonella* dam double mutant candidates were classified into two groups, Class I: those that showed similar colonization/persistence relative to that of the parental *S. Typhimurium* UK-1 damΔ232 single mutant vaccine strain (dam mgtC; dam sifA; dam spvB); and Class II: those that exhibited colonization/persistence relative to that exhibited by the parental *Salmonella* dam vaccine (dam aroA, dam htrA, dam spiC, dam ssaV). These data indicate that Class I vaccine candidates vaccines sustained a low grade persistence in host tissues, whereas Class II vaccines showed rapid clearance in vaccinated animals.

2.3. Efficacy Evaluation of *Salmonella* Dam Double Mutant Vaccine Candidates

Figure 2:
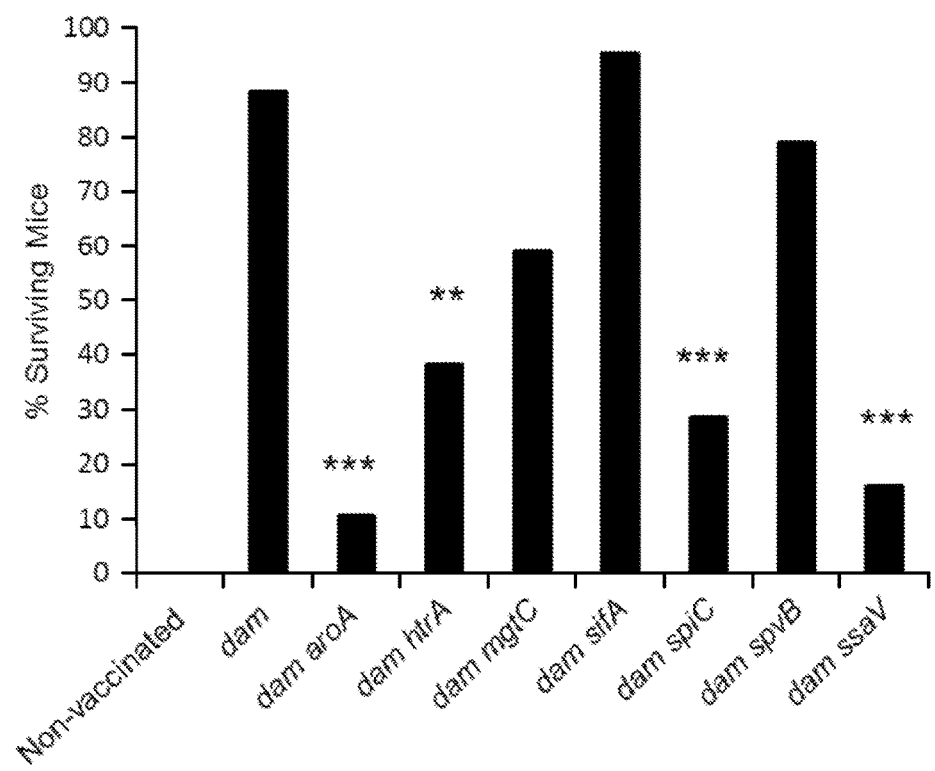

The *Salmonella* dam double mutant vaccine candidates (Class I and Class II) were examined to discern whether a low-grade persistence is necessary to confer protective immune responses similar to that elicited by the parental *Salmonella* dam vaccine. BALB/c mice were orally immunized with each of the seven *Salmonella* dam double mutant vaccine candidates ($10^9$ CFU). To avoid transient, non-specific cross-protective immune responses attributed to the persistence of the vaccine strain within host tissues [23-25], immunized mice were not challenged with virulent *Salmonella* until 4 to 5 weeks after the vaccine strain was cleared from mucosal (Peyer's patches; mesenteric lymph nodes) and systemic tissues (liver; spleen) of immunized animals. Eleven weeks post-immunization, mice were orally challenged with a 200-fold $LD_{50}$ infection dose with the virulent parental strain, *S. Typhimurium* UK-1. Mice immunized with all (3 of 3) Class I vaccine candidates (dam mgtC, dam sifA, dam spvB) exhibited robust protection against virulent homologous challenge, similar to that exhibited by the parental *S. Typhimurium* UK-1 damΔ232 strain (FIG. 2). Conversely, none (0 of 4) of the Class II vaccine candidates (dam aroA, dam htrA, dam spiC, dam ssaV) that exhibited accelerated clearance conferred significant protection to virulent homologous challenge in comparison to the parental *S. Typhimurium* UK-1 damΔ232 strain (P<0.01, * P<0.001).

Figure 3:
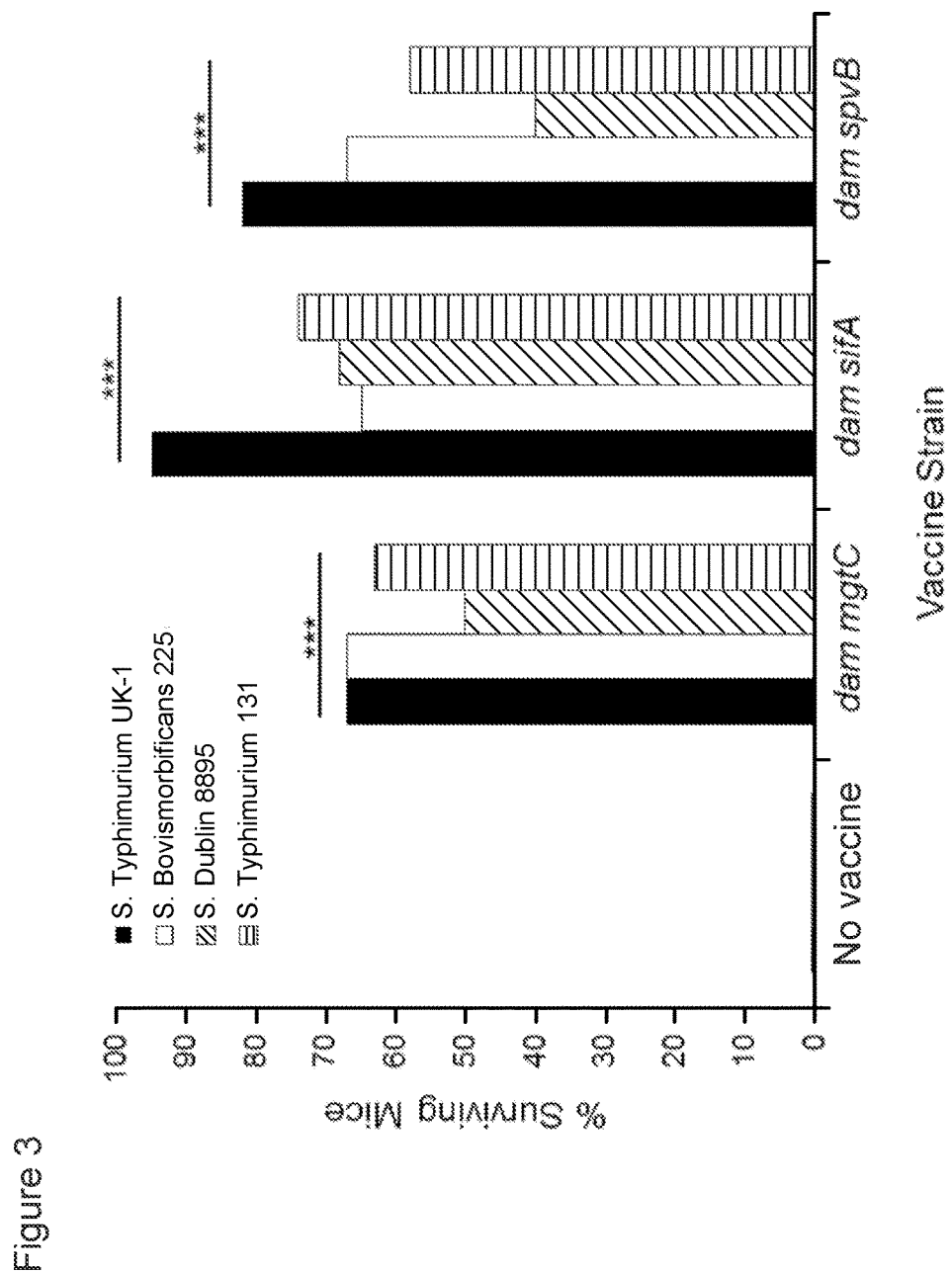

Class I vaccine candidates were assessed for the capacity to elicit cross-protection to heterologous strains as has been shown for *Salmonella* dam vaccine strains in murine [2, 9], avian [10, 11], ovine [12] and bovine [13-15] models of salmonellosis. BALB/c mice were orally immunized with Class I vaccine candidates (dam mgtC, dam sifA, or dam spvB; $10^9$ CFU). Eleven weeks post-immunization, mice were challenged with livestock-industry relevant pathogenic *Salmonella* strains derived from sheep (*S. Bovismorbificans* 174, *S. Typhimurium* 131) and cattle (*S. Dublin* 8895), comprising serogroups C2-C3, B, and D, respectively. All 3 Class I vaccine candidates conferred robust cross-protection to the three heterologous virulent strains tested (FIG. 3; *** P<0.001), similar to the levels of cross-protection exhibited previously against these 3 heterologous challenge strains in mice vaccinated with a *S. Typhimurium* 14028 damΔ232 vaccine strain [2]. These data are consistent with the hypothesis that the low grade persistence of Class I vaccine candidates in host tissues (dam mgtC, dam sifA, and dam spvB) may provide a stable source of antigens over the time needed to transition to the development of strong adaptive immune responses [2,9,19].

2.4. Vaccine Safety Evaluation Via Assessment of Reversion to 2-AP Resistance.

Reversion to heightened virulence is a concern for all modified live vaccines. *Salmonella* dam mutant vaccines have the capacity to undergo reversion to a more virulent state after i.p. (but not oral) infection via acquisition of a mutation(s) in methyl-directed mismatch repair genes [29]. Such reversion can be evaluated using the purine analog 2-amino purine (2-AP), which is toxic to bacteria lacking Dam function [21]. That is, the parental dam strain (2-AP$^s$) can be assessed for reversion to 2-AP$^r$ (as a potential indicator of heightened virulence) in systemic tissues [29]. BALB/c mice were i.p. infected with *Salmonella* dam double mutant vaccine candidates, dam mgtC, dam sifA, dam spvB. or parental *S. Typhimurium* UK-1 damΔ232 strain ($10^3$ CFU). Five days post infection, bacteria recovered from the liver and spleen were assessed for 2-AP$^s$ (persistence) and reversion to the 2-AP$^r$ phenotype (FIG. 4). All 3 vaccine candidates (dam mgtC, dam sifA, dam spvB) showed significantly reduced colonization/persistence (2-AP$^s$) and reduced reversion to 2-AP resistance relative in the spleen/liver relative to that of the parental *S. Typhimurium* UK-1 damΔ232 strain (* P<0.05).

2-AP$^r$ derivatives of *Salmonella* dam double mutant vaccine candidates and the parental dam UK-1 vaccine isolated from the spleens of infected mice were evaluated via oral and i.p. lethal dose ($LD_{50}$) virulence assays. The oral and i.p. $LD_{50}$ for wild-type UK-1 are $10^5$ and <10 CFU, respectively. The oral $LD_{50}$ of all 2-AP$^r$ isolates derived from all *Salmonella* dam double mutant vaccine candidates (11 of 11) or parental *Salmonella* dam vaccine (5 of 5) were avirulent by oral administration (Table 2). In contrast, all (11 of 11) 2-AP$^r$ isolates derived from *Salmonella* dam double mutant vaccine candidates were highly attenuated via i.p. infection, whereas those derived from the parental dam vaccine (5 of 5) were associated with reversion to a more virulent state, as demonstrated previously [29]. These data indicate that *Salmonella* dam mgtC, dam sifA, and dam spvB vaccine strains exhibited significantly improved vaccine safety as evidenced by the failure to give rise to virulent revertants during the infective process, contrary to the *Salmonella* dam vaccine.

2.5. Vaccine and Challenge Strain Shedding Evaluation of *Salmonella* Dam Double Mutant Vaccine Strains Reduced vaccine and challenge strain shedding in vaccinated animals are desired traits for vaccine safety. Kanamycin-resistant derivatives of *S. Typhimurium* UK-1 damΔ232 double mutant vaccine candidates were constructed used to assess vaccine strain and challenge strain shedding in the feces of immunized animals. BALB/c mice were immunized with either *Salmonella* dam double mutant vaccine candidates (dam mgtC [MT3183]; dam sifA [MT3184]; dam spvB [MT3186]) or the dam UK-1 parent strain (MT3180) by the oral route ($10^9$ CFU). Vaccine strain shedding. Fecal pellets were obtained and assessed for Kn$^r$ bacteria at Days 2, 4, 7, 11, 14, and 21 post-infection. All *Salmonella* dam double deletion vaccine candidates exhibited significantly reduced vaccine strain fecal shedding in comparison to that of the parental *S. Typhimurium* UK-1 damΔ232 strain (FIG. 5; P<0.05). Challenge strain shedding. Eleven weeks post-immunization, vaccinated mice were challenged with a dose of 100 $LD_{50}$ of Kn$^r$ derivative of *S. Typhimurium* UK-1 (MT2315; $10^7$ CFU). Fecal pellets were obtained and assessed for Kn$^r$ bacteria at Days 2, 4, 7, 11, 14, and 21 post-infection. *Salmonella* dam mgtC, dam sifA and dam spvB strains exhibited a significantly reduction in challenge strain shedding relative to that of the parental *S. Typhimurium* UK-1 damΔ232 vaccine over a 3 week period, with dam sifA and dam spvB strains showing reduced shedding from day 4 to 21 (FIG. 6; P<0.05). These data indicate that vaccination with *Salmonella* dam double mutant vaccines results in less vaccine fecal shedding relative to that of the parental *Salmonella* dam vaccine and double deletion vaccination provides more robust attenuation of wildtype *salmonella* shedding following virulent challenge than the dam parent vaccine.

2.6. Environmental Persistence (De-Ionized Water and Sheep Feces) Evaluation of *Salmonella* Dam Double Mutant Vaccine Strains

*Salmonella* dam double mutant vaccine candidates were evaluated for environmental persistence in de-ionized water and in sheep feces. De-ionized water. Deionized water was inoculated with Kn$^r$ derivatives of either *Salmonella* dam double mutant vaccine candidates (dam mgtC [MT3183]; dam sifA [MT3184]; dam spvB [MT3186]) or the dam UK-1 parent strain (MT3180) ($10^4$ CFU/ml) (FIG. 7). Water samples were plated for CFU/g over a two week period. All (3 of 3) *Salmonella* dam double mutant vaccine candidates and the parental dam strain showed significantly reduced viability in de-ionized water over the 2 week incubation in comparison to that of the wildtypeUK-1 strain (FIG. 7; P<0.05). Further, the low-level vaccine persistence in water may be compatible with trough water vaccine administration. Sheep feces. Twenty percent dry matter sheep feces was inoculated with Kn$^r$ derivatives of either *Salmonella* dam double mutant vaccine candidates (dam mgtC [MT3183]; dam sifA [MT3184]; dam spvB [MT3186]) or the dam UK-1 parent strain (MT3180) (10$^4$ CFU/ml). Fecal samples were plated for CFU/g over a two week period. All (3 of 3) *Salmonella* dam double mutant vaccine candidates showed significantly reduced viability in sheep feces over the 2 week incubation in comparison to that of the wildtype UK-1 strain over the 2 week incubation period (FIG. 8; P<0.05). Further, *Salmonella* dam sifA showed significantly reduced viability in sheep feces relative to that of the other 3 vaccine strains tests (P<0.05). These data indicate that *Salmonella* vaccine candidates show reduced environmental persistence in both de-ionized water and sheep feces in comparison to that of the wild type UK-1 strain.

3. Discussion

Despite good husbandry practices, salmonellosis continues to be a significant problem in intensive production systems that favor fecal-oral transmission. Disease is principally caused by increased pathogen exposure and disease susceptibility. Fluctuations in environmental conditions cause shifts in the environmental pathogen load and subsequently host challenge. Physiological changes associated with pregnancy and parturition increase susceptibility to disease as does the naïve immune status of neonates. Management practices may also negatively impact on host immunity with cumulative stressors experienced by stock on farm (mustering, yarding, food and water deprivation prior to transport), during transport (food and water deprivation, environmental stress), and in sale yards (co-mingling, pathogen exposure).

Livestock vaccination against salmonellosis is a viable approach to prevent disease since it prevents contamination of food and water supplies at the outset, resulting in diminished pathogen exposure, transmission, animal disease, and the direct contamination of livestock-derived food products and indirect contamination of fruit and vegetable food products by contaminated water.

Optimally, livestock should be vaccinated on farms of origin to elicit immunity before livestock experience the stressors and pathogen exposure associated with sale, transport, and the high-risk period following entry into the feedlot. The challenge is convincing producers, who supply stock to feedlots, to vaccinate the animals prior to sale since the cost of disease is not incurred on the property of origin, resulting in the current practice of livestock immunization during the high risk period immediately following entry into the feedlot.

If an affordable and effective product is made available to the commercial sector, the vaccine could be applied broadly across animal production industries as vaccination is simple, understood by producers, and likely to be adopted and, thus, may play a critical role in the success of any comprehensive food safety plan.

As a potential means to address this issue, modified live *Salmonella* dam vaccines have been shown to be effective and well-tolerated in immunized stock [10-15], and can be administered via drinking water [12, 16]. However, the principal concerns of live vaccines are safety, shedding, and environmental persistence.

Herein, secondary virulence-attenuating mutations were introduced into a *Salmonella* dam strain to screen for vaccine candidates that were safe in the animal and the environment, and maintained the capacity to confer cross-protective efficacy. *S. Typhimurium* dam sifA exhibited improved vaccine safety, reduced vaccine and challenge strain shedding, reduced environmental persistence, and conferred a low grade persistence in host tissues that was sufficient to confer cross-protection to heterologous pathogenic salmonellae serotypes derived from infected livestock [31]. These data indicate that *Salmonella* dam sifA exhibits a favorable therapeutic index (safety/efficacy) for commercial applications, supporting improved safety in both vaccinates and the environment, along with the capacity to elicit cross-protective immunity against pathogenic serotypes.

Herein, the safety of the vaccine was evaluated in vaccinated animals and in conditions mimicking the environment. *Salmonella* dam mgtC, dam sifA, and dam spvB vaccine strains sustained a low grade persistence in host tissues that was associated with the maintenance of cross-protective immunity against heterologous pathogenic serotypes derived from infected stock. Further, the *Salmonella* dam sifA vaccines exhibited improved vaccine safety (vaccine shedding; challenge strain shedding; persistence in systemic tissues; persistence in the environment), while maintaining robust efficacy against virulence challenge with homologous and heterologous pathogenic serotypes. Thus, the *Salmonella* dam sifA vaccine candidate exhibits considerable increased safety without compromising cross-protective efficacy and may prove to be a safe, effective, and low cost means of oral dosing of livestock without significant environmental persistence.

TABLE 1

Bacterial strains used in this study

| Strain | Genotype | Source/Reference |
| --- | --- | --- |
| *S. Typhimurium* UK-1 | | |
| χ3761 | Wild type (chicken) | [17] |
| MT2315 | zjf7504::MudJ (Kn$^r$) | [10] |
| MT3134 | Δdam232 | This work |
| MT3138 | Δdam232 ΔaroA | This work |
| MT3142 | Δdam232 ΔhtrA | This work |
| MT3146 | Δdam232 ΔmgtC | This work |
| MT3150 | Δdam232 ΔsifA | This work |
| MT3154 | Δdam232 ΔspiC | This work |
| MT3158 | Δdam232 ΔspvB | This work |
| MT3162 | Δdam232 ΔssaV | This work |
| MT3180 | Δdam232 zjf7504::MudJ (Kn$^r$) | This work |
| MT3183 | Δdam232 ΔmgtC zjf7504::MudJ (Kn$^r$) | This work |
| MT3184 | Δdam232 ΔsifA zjf7504::MudJ (Kn$^r$) | This work |
| MT3186 | Δdam232 ΔspvB zjf7504::MudJ (Kn$^r$) | This work |
| Animal isolates | | |
| 131 | *S. Typhimurium* (sheep) | [31] |
| 225 | *S. Bovismorbificans* (sheep) | [31] |
| 8895 | *S. Dublin* cattle isolate (cattle) | [31] |

TABLE 2

In vivo-selected 2-AP$^r$ derivatives of dam double mutant Salmonella are avirulent via the intraperitoneal or oral routes of infection

| Challenge strain | Relevant genotype | IP Virulence $(LD_{50})^a$ | Oral Virulence $(LD_{50})$ |
|---|---|---|---|
| S. Typhimurium UK-1 | Wild type | <10 | $10^5$ |
| MT3134 | Δdam232 | >$10^4$ | ≥$10^{10}$ |
| MT3243 | Δdam232 2-AP$^r$ isolate #1 | ≥$10^3$ | $10^9$-$10^{10}$ |
| MT3244 | Δdam232 2-AP$^r$ isolate #2 | <$10^2$ | $10^9$ |
| MT3245 | Δdam232 2-AP$^r$ isolate #3 | <$10^2$ | $10^9$ |
| MT3246 | Δdam232 2-AP$^r$ isolate #4 | <$10^2$ | $10^9$ |
| MT3247 | Δdam232 2-AP$^r$ isolate #5 | <$10^2$ | ≥$10^{10}$ |
| MT3146 | Δdam232 ΔmgtC | >$10^4$ | ≥$10^{10}$ |
| MT3248 | Δdam232 ΔmgtC 2-AP$^r$ isolate #1 | $10^3$ | ≥$10^{10}$ |
| MT3249 | Δdam232 ΔmgtC 2-AP$^r$ isolate #2 | ≥$10^4$ | ≥$10^{10}$ |
| MT3250 | Δdam232 ΔmgtC 2-AP$^r$ isolate #3 | ≥$10^4$ | $10^9$-$10^{10}$ |
| MT3150 | Δdam232 ΔsifA | >$10^4$ | ≥$10^{10}$ |
| MT3251 | Δdam232 ΔsifA 2-AP$^r$ isolate #1 | ≥$10^4$ | ≥$10^{10}$ |
| MT3252 | Δdam232 ΔsifA 2-AP$^r$ isolate #2 | ≥$10^4$ | $10^9$-$10^{10}$ |
| MT3253 | Δdam232 ΔsifA 2-AP$^r$ isolate #3 | ≥$10^4$ | ≥$10^{10}$ |
| MT3254 | Δdam232 ΔsifA 2-AP$^r$ isolate #4 | ≥$10^4$ | $10^9$-$10^{10}$ |
| MT3255 | Δdam232 ΔsifA 2-AP$^r$ isolate #5 | ≥$10^4$ | ≥$10^{10}$ |
| MT3158 | Δdam232 ΔspvB | >$10^4$ | ≥$10^{10}$ |
| MT3256 | Δdam232 ΔspvB 2-AP$^r$ isolate #1 | ≥$10^4$ | ≥$10^{10}$ |
| MT3257 | Δdam232 ΔspvB 2-AP$^r$ isolate #2 | ≥$10^4$ | $10^9$-$10^{10}$ |
| MT3258 | Δdam232 ΔspvB 2-AP$^r$ isolate #3 | ≥$10^4$ | $10^9$-$10^{10}$ |

$^a$Independently isolated, in vivo selected, 2-amino purine resistant (2-AP$^r$) derivatives of *Salmonella* dam mutant vaccines strains were isolated from the spleens of infected mice, and evaluated for oral and intraperitoneal (IP) virulence in naïve mice [29]. The $LD_{50}$ assay for each of these strains was compared to that of the wild type (UK-1). The IP $LD_{50}$ was determined by infecting five mice per challenge dose; the peroral $LD_{50}$ via gastrointubation was determined by infecting ten mice per challenge dose. The oral and i.p. $LD_{50}$s for wild-type UK-1 are $10^5$ and <10 CFU, respectively [30]. Surviving mice were scored >2 weeks post-infection.

REFERENCES

[1] Mahan M J, Heithoff D M, House J K. *Salmonella* cross-protective vaccines: fast-forward to the next generation of food safety. Future Microbiol. 2012; 7:805-8.

[2] Heithoff D M, Enioutina E Y, Bareyan D, Daynes R A, Mahan M J. Conditions that diminish myeloid-derived suppressor cell activities stimulate cross-protective immunity. Infect Immun. 2008; 76:5191-9.

[3] Hegazy W A H, Hensel M. *Salmonella enterica* as a vaccine carrier. Future Microbiol. 2012; 7:111-27.

[4] Kong Q, Yang J, Liu Q, Alamuri P, Roland K L, Curtiss III R. Effect of deletion of genes involved in lipopolysaccharide core and O-antigen synthesis on virulence and immunogenicity of *Salmonella enterica* serovar Typhimurium. Infect Immun. 2011; 79:4227-39.

[5] Li Y, Wang S, Scarpellini G, Gunn B, Xin W, Wanda S Y, et al. Evaluation of new generation *Salmonella enterica* serovar Typhimurium vaccines with regulated delayed attenuation to induce immune responses against PspA. Proc Natl Acad Sci USA. 2009; 106:593-8.

[6] Nagy G, Palkovics T, Otto A, Kusch H, Kocsis B, Dobrindt U, et al. "Gently rough": the vaccine potential of a *Salmonella enterica* regulatory lipopolysaccharide mutant. J Infect Dis. 2008; 198:1699-706.

[7] Curtiss R, Xin W, Yuhua L, Kong W, Wanda S Y, Gunn B, et al. New technologies in using recombinant attenuated *Salmonella* vaccine vectors. Crit Rev Immunol. 2010; 30:255-70.

[8] Singh B. *Salmonella* vaccines for animals and birds and their future perspective. Open Vaccine J. 2009; 2:100-12.

[9] Heithoff D M, Enioutina E Y, Daynes R A, Sinsheimer R L, Low D A, Mahan M J. *Salmonella* DNA adenine methylase mutants confer cross-protective immunity. Infect Immun. 2001; 69:6725-30.

[10] Dueger E L, House J K, Heithoff D M, Mahan M J. *Salmonella* DNA adenine methylase mutants elicit protective immune responses to homologous and heterologous serovars in chickens. Infect Immun. 2001; 69:7950-4.

[11] Dueger E L, House J K, Heithoff D M, Mahan M J. *Salmonella* DNA adenine methylase mutants prevent colonization of newly hatched chickens by homologous and heterologous serovars. Intl J Food Microbiol. 2003a; 80:153-9.

[12] Mohler V L, Heithoff D M, Mahan M J, Walker K H, Hornitzky M A, Gabor L, et al. Protective immunity conferred by a DNA adenine methylase deficient *Salmonella enterica* serovar Typhimurium vaccine when delivered in-water to sheep challenged with *Salmonella enterica* serovar Typhimurium. Vaccine. 2011; 29:3571-82.

[13] Dueger E L, House J K, Heithoff D M, Mahan M J. *Salmonella* DNA adenine methylase mutants elicit early and late onset protective immune responses in calves. Vaccine. 2003; 21:3249-58.

[14] Mohler V, Heithoff D, Mahan M, Walker K, Hornitzky M, McConnell C, et al. Cross-protective immunity in calves conferred by a DNA adenine methylase deficient *Salmonella enterica* serovar Typhimurium vaccine. Vaccine. 2006; 24:1339.

[15] Mohler V, Heithoff D, Mahan M, Walker K, Hornitzky M, Shum L, et al. Cross-protective immunity conferred by a DNA adenine methylase deficient *Salmonella enterica* serovar Typhimurium vaccine in calves challenged with *Salmonella* serovar Newport. Vaccine. 2008; 26:1751-8.

[16] Mohler V, Heithoff D, Mahan M, Hornitzky M, Thomson P, House J. Development of a novel in-water vaccination protocol for DNA adenine methylase deficient *Salmonella enterica* serovar Typhimurium vaccine in adult sheep. Vaccine. 2012; 30:1481-91.

[17] Hassan J O, Curtiss R, 3rd. Development and evaluation of an experimental vaccination program using a live avirulent *Salmonella typhimurium* strain to protect immunized chickens against challenge with homologous and heterologous *Salmonella* serotypes. Infect Immun. 1994; 62:5519-27.

[18] Davis R W, Botstein D, Roth J R. Advanced bacterial genetics. Plainview, N.Y.: Cold Spring Harbor Laboratory Press; 1980.

[19] Heithoff D M, Sinsheimer R L, Low D A, Mahan M J. An essential role for DNA adenine methylation in bacterial virulence [see comments]. Science. 1999; 284:967-70.

[20] Donnenberg M S, Kaper J B. Construction of an eae deletion mutant of enteropathogenic *Escherichia coli* by using a positive-selection suicide vector. Infect Immun. 1991; 59:4310-7.

[21] Glickman B, van den Elsen P, Radman M. Induced mutagenesis in dam-mutants of *Escherichia coli*: a role for 6-methyladenine residues in mutation avoidance. Mol Gen Genet. 1978; 163:307-12.

[22] Julio S, Heithoff D, Provenzano D, Klose K, Sinsheimer R, Low D, et al. DNA Adenine methylase is essential for viability and plays a role in the pathogenesis of *Yersinia pseudotuberculosis* and *Vibrio cholerae*. Infect Immun. 2001; 69:7610-5.

[23] Harrison J A, Villarreal-Ramos B, Mastroeni P, Demarco de Hormaeche R, Hormaeche C E. Correlates of protection induced by live Aro-*Salmonella typhimurium* vaccines in the murine typhoid model. Immunology. 1997; 90:618-25.

[24] Hormaeche C E, Joysey H S, Desilva L, lzhar M, Stocker B A. Immunity conferred by Aro-*Salmonella* live vaccines. Microb Pathog. 1991; 10:149-58.

[25] Hormaeche C E, Mastroeni P, Harrison J A, Demarco de Hormaeche R, Svenson S, Stocker B A. Protection against oral challenge three months after i.v. immunization of BALB/c mice with live Aro *Salmonella typhimurium* and *Salmonella enteritidis* vaccines is serotype (species)-dependent and only partially determined by the main LPS O antigen. Vaccine. 1996; 14:251-9.

[26] Conner C P, Heithoff D M, Julio S M, R. L. S, Mahan M J. Differential patterns of acquired virulence genes distinguish *Salmonella* strains. Proc Natl Acad Sci USA 1998; 95:4641-5.

[27] Griggs T. Determining forage dry matter concentration with a microwave oven A G/Forage & Pasture/2005-01. 2005.

[28] Pitt R, Brusewitz G, Chase L, Collins M. Forage moisture determination. NRAES (59)(Cooperative Extension). 1993.

[29] Heithoff D, Badie G, Julio S, Enioutina E, Daynes R, Sinsheimer R, et al. In vivo-selected mutations in methyl-directed mismatch repair suppress the virulence attenuation of *Salmonella* dam mutant strains following intraperitoneal, but not oral, infection of naïve mice. J Bacteriol. 2007; 189:4708-17.

[30] Heithoff D M, Shimp W R, House J K, Xie Y, Weimer B C, Sinsheimer R L, et al. Intraspecies variation in the emergence of hyperinfectious bacterial strains in nature. PLoS Pathogens. 2012; 8:e1002647.

[31] Heithoff D M, Shimp W R, Lau P W, Badie G, Enioutina E Y, Daynes R A, et al. Human *Salmonella* clinical isolates distinct from those of animal origin. Appl Environ Microbiol. 2008; 74:1757-66.

[32] Griggs T. Determining forage dry matter concentration with a microwave oven A G/Forage & Pasture/2005-01. 2005.

[33] Pitt R, Brusewitz G, Chase L, Collins M. Forage moisture determination. NRAES (59)(Cooperative Extension). 1993.

[34] International V. GenStat for Windows 15$^{th}$ Edition VSN International, Hemel Hempstead, U K. 2012.

The invention claimed is:

1. A *Salmonella* microorganism, wherein
the microorganism is selected from the group consisting of
*Salmonella enterica* serovar *S. Typhimurium, S. Enteritidis, S. Choleraesuis*, or *S. Bovismorbificans* comprising a loss of function mutation in the dam gene and at least one further loss of function mutation in a gene selected from the group consisting of: sifA, spvB and mgtC;
*Salmonella enterica* serovar *Dublin* comprising a loss of function mutation in the dam gene and at least one further loss of function mutation in a gene selected from the group consisting of spvB and mgtC; and
*Salmonella enterica* serovar *S. Newport* comprising a loss of function mutation in the dam gene and at least one further loss of function mutation in a gene selected from the group consisting of: sifA and mgtC.

2. The *Salmonella* microorganism of claim 1, wherein the at least one further loss of function mutation is in the sifA gene.

3. The *Salmonella* microorganism of claim 1, wherein each loss of function mutation is selected from the group consisting of an insertion, a deletion and/or substitution of one or more nucleotides in the mutated gene.

4. The *Salmonella*-microorganism of claim 1, wherein the serovar is *S. Typhimurium*.

5. A composition for inducing an immune response in a subject to a *Salmonella* microorganism, said composition comprising
a microorganism selected from the group consisting of
*Salmonella enterica* serovar *S. Typhimurium, S. Enteritidis, S. Choleraesuis*, or *S. Bovismorbificans* comprising a loss of function mutation in the dam gene and at least one further loss of function mutation in a gene selected from the group consisting of: sifA, spvB and mgtC;
*Salmonella enterica* serovar *Dublin* comprising a loss of function mutation in the dam gene and at least one further loss of function mutation in a gene selected from the group consisting of spvB and mgtC; and
*Salmonella enterica* serovar *S. Newport* comprising a loss of function mutation in the dam gene and at least one further loss of function mutation in a gene selected from the group consisting of: sifA and mgtC; and
one or more secondary compositions comprising an adjuvant, a diluent comprising a buffer, a carrier or an excipient.

6. The composition of claim 5, wherein
the at least one further loss of function mutation is in the sifA gene.

7. The composition of claim 5, wherein
each loss of function mutation is selected from the group consisting of an insertion, a deletion and/or substitution of one or more nucleotides in the mutated gene.

8. The composition of claim 5, wherein,
the serovar is *S. Typhimurium*.

9. A purified culture of *Salmonella* microorganism, wherein the *Salmonella* microorganism selected from the group consisting of

*Salmonella enterica* serovar *S. Typhimurium, S. Enteritidis, S. Choleraesuis*, or *S. Bovismorbificans* comprising a loss of function mutation in the dam gene and at least one further loss of function mutation in a gene selected from the group consisting of: sifA, spvB and mgtC;

*Salmonella enterica* serovar *Dublin* comprising a loss of function mutation in the dam gene and at least one further loss of function mutation in a gene selected from the group consisting of spvB and mgtC; and

*Salmonella enterica* serovar *S. Newport* comprising a loss of function mutation in the dam gene and at least one further loss of function mutation in a gene selected from the group consisting of: sifA and mgtC.

10. The purified culture of claim 9 wherein the culture is freeze dried, frozen, or reconstituted.

11. The purified culture of claim 9, wherein the at least one further loss of function mutation is in the sifA gene.

12. The purified culture of claim 9, wherein each loss of function mutation is selected from the group consisting of an insertion, a deletion and/or substitution of one or more nucleotides in the mutated gene.

13. The purified culture of claim 9, wherein the serovar is *S. Typhimurium.*

14. A method of preventing or reducing the likelihood of infection of a subject with a virulent *Salmonella* microorganism, comprising administering to the subject an amount of *Salmonella* microorganism, wherein the *Salmonella* microorganism is serovar *S. Typhimurium* and comprises a loss of function mutation in the dam gene and at least one further loss of function mutation in a gene selected from the group consisting of: sifA, spvB and mgtC; and wherein the amount of *Salmonella* microorganism administered is sufficient to elicit an immune response in the subject.

15. The method of claim 14, wherein the at least one further loss of function mutation is in the sifA gene.

16. The method of claim 14, wherein each loss of function mutation is selected from the group consisting of an insertion, a deletion and/or substitution of one or more nucleotides in the mutated gene.

17. The method of claim 14, wherein the *Salmonella* microorganism is administered in the form of a composition comprising *Salmonella* microorganism and an adjuvant, diluent, carrier or excipient.

18. The method of claim 14, wherein the *Salmonella* microorganism is administered in the form of a purified culture.

19. The method of claim 14, wherein the *Salmonella* microorganism is administered via the oral, nasal or parenteral routes.

20. The method of claim 14, wherein the subject is a human subject.

21. The method of claim 14, wherein the subject is a veterinary species.

22. The method of claim 21, wherein the subject is selected from the group consisting of cow, horse, goat, sheep, pig and poultry.

23. The composition of claim 1, wherein the one or more secondary compositions comprises a diluent comprising a buffer and the buffer comprises a buffer selected from the group consisting of: citrate buffer containing sucrose; bicarbonate buffer; and bicarbonate buffer comprising ascorbic acid, lactose, and/or aspartame.

24. The composition of claim 1, wherein the one or more secondary compositions comprises a carrier comprising a protein, a sugar, or polyvinylpyrrolidone.

25. The composition of claim 24, wherein the carrier comprises skim milk protein or sucrose.

* * * * *